United States Patent [19]

Chari et al.

[11] Patent Number: 5,846,545
[45] Date of Patent: Dec. 8, 1998

[54] TARGETED DELIVERY OF CYCLOPROPYLBENZINDOLE-CONTAINING CYTOTOXIC DRUGS

[75] Inventors: Ravi V. J. Chari, St. Newton; Viktor S. Goldmakher, Newton Center; Walter A. Blattler, Brookline, all of Mass.

[73] Assignee: Immunogen, Inc., Cambridge, Mass.

[21] Appl. No.: 468,306

[22] Filed: Jun. 6, 1995

Related U.S. Application Data

[63] Continuation of Ser. No. 210,742, Mar. 21, 1994, Pat. No. 5,475,092, which is a continuation of Ser. No. 857,171, Mar. 25, 1992, abandoned.

[51] Int. Cl.$^6$ .................................................. A61K 38/18
[52] U.S. Cl. .................................. 424/195.11; 424/194.1; 424/193.1; 424/198.1; 424/178.1; 530/399; 530/391.7; 530/391.9
[58] Field of Search .............................. 424/178.1, 179.1, 424/195.11, 181.1, 194.1, 198.1, 193.1; 530/391.7, 391.9, 399; 548/420, 427, 430, 433

[56] References Cited

U.S. PATENT DOCUMENTS

| | | | |
|---|---|---|---|
| 4,169,888 | 10/1979 | Hanka et al. | 424/121 |
| 4,301,248 | 11/1981 | Nettleton et al. | 435/119 |
| 4,912,227 | 3/1990 | Kelley et al. | 548/421 |
| 5,045,451 | 9/1991 | Uhr et al. | 435/7.23 |
| 5,087,616 | 2/1992 | Myers et al. | 514/21 |
| 5,106,951 | 4/1992 | Morgan et al. | 530/391.9 |
| 5,135,736 | 8/1992 | Anderson et al. | 424/1.1 |

FOREIGN PATENT DOCUMENTS

| | | |
|---|---|---|
| 1238907 | 7/1988 | Canada . |
| 0154445 | 9/1985 | European Pat. Off. . |
| 0359454 | 3/1990 | European Pat. Off. . |
| 2405956 | 5/1979 | France . |
| 2461001 | 1/1981 | France . |
| 2841361 | 4/1979 | Germany . |
| 5464695 | 5/1979 | Japan . |
| 60-193989 | 2/1985 | Japan . |
| 7809639 | 4/1979 | Netherlands . |
| 643564 | 6/1984 | Switzerland . |
| 797591 | 1/1981 | U.S.S.R. . |
| 2008088 | 5/1979 | United Kingdom . |
| 8804659 | 6/1988 | WIPO . |
| 9002746 | 3/1990 | WIPO . |
| 9008838 | 8/1990 | WIPO . |
| 9116324 | 10/1991 | WIPO . |

OTHER PUBLICATIONS

Boyer et al., *Antibody, Innumoconjugates and Radiopharmaceuticals*, vol. 1, No. 2, pp. 105–162, 1988.
Waldmann, *Science*, vol. 252, pp. 1657–1662 (1991).
Roitt et al., *Immunology*, 3rd Edition, Mosby, St. Louis, pp. 17–19 (1993).
Osband et al., *Immunology Today*, vol. 11, No. 6, 1990, pp. 193–195.
U.S.A.N. 07/513,501, Paul A. Aristoff et al, *Novel CC–1065 Analogs*, Oct. 31, 1991, pp. 1–119, (publically available from WIPO).
Hermentin et al., Behring Inst. Mitt., No. 82, pp. 197–215 (1988).
Pierce Catalog, pp. E10–E45 (1992).
Carroll and Greene, Antibodies in Radiodiagnosis and Therapy, Zalutsky (Ed.) CRC Press, Boca Raton, Florida, pp. 13–43 (1989).
Coulter Catalog, pp. 27,34–35 and 40–41 (1992).
Pierce Catalog, pp. E10–E15, E20 and E44 (1991).
Kirkwood et al., Journal of Clinical Onocology, vol. 5, No. 8, pp. 1247–1255 (1987).
Murray et al., J. Nucl. Med., vol. 28, pp. 25–33 (1987).
Coulter Catalog, pp. 5–6, (1992).
Borrebaeck, Journal of Immunological Methods, vol. 123, pp. 157–165 (1989).
Boger et al., Bioorganic & Medicinal Chemistry Letters, vol. 1, No. 2, pp. 115–120 (1991).
Reynolds et al., "The Chemistry Mechanism of Action and Biological Properties of CC–1065 A Potent Antitumor Antibiotic", Mar. 1986, pp. 319–334 (The Jour. of Antibiotics, vol. XXXIX, No. 3).
Martin et al., "CC–1065 Transformations", Jun. 1985, pp. 745–752, *The Journal of Antibiotics*, vol. XXXVIII, No. 6.
Warpehoski et al., "Stereoelectronic Factors Influencing the Biological Acitivity and DNA Interaction of Synthetic Antitumor Agents Modeled on CC–1065", 1988, pp. 590–603, *J. Med. Chem.*, 31.
Ravi et al., "Immunoconjugates Containing Novel Maytansinoids: Promising Anticancer Drugs", Jan. 1, 1992, pp. 127–131, *Cancer Research*, 52.
Boger et al., A Potent, Simple Derivative of an Analog of the CC1065 Alkylation Subunit, 1991, pp. 55–58, *Bioorganic & Medicinal Chemistry Letters*, vol. 1, No. 1.
McGovren et al., "Preliminary Toxicity Studies with the DNA–Binding Antibiotic, CC–1065", Jan. 1984, pp. 63–70, *The Journal of Antibiotics*, vol. XXXVII, No. 1.
Hanaka et al., "CC–1065 (NSC–298223), A new Antitumor Antiobiotic Production, In Vitro Biological Activity, Microbiological Assays and Taxonomy of the Producing Microoranism", Dec. 1978, pp. 1211–1217, *The Journal of Antibiotics*, vol. XXXI, No. 12.
Gomi et al., "Anticellular and Antitumor Activity of Duocarmycons Novel Antitumor Antibiotics", JPN *J. Cancer Res.*, vol. 83, No. 1, pp. 113–120, 1992.

(List continued on next page.)

*Primary Examiner*—Ponnathapura Achutamurthy
*Assistant Examiner*—J. D. Wessendorf
*Attorney, Agent, or Firm*—Sughrue, Mion, Zinn, Macpeak & Seas, PLLC

[57] ABSTRACT

Gytotoxic agents containing a cell binding agent chemically linked to one or more analogue or derivative of CC-1065 are described. The therapeutic use of the cytotoxic agents is also described. These cytotoxic agents have therapeutic use because they deliver the cytotoxic drugs to a specific cell population in a targeted fashion.

57 Claims, 8 Drawing Sheets

OTHER PUBLICATIONS

Riganti et al., "The Unique Interaction with Immunity of FCE 24517, an Antitumor Drug with a Novel Mode of Action", *Int. J. Immunopharm.*, (United Kingdom), vol. 14, No. 2, pp. 239–251, 1992.

Lee et al., "Determination of the Structural Features of (+)–CC–1065 that are Responsible for Bending and Winding of DNA", *Chem. Res. Toxicol.*, (USA), vol. 4, No. 2, pp. 203–213, 1991.

Swenson et al., "Evaluation of DNA binding characteristics of some CC–1065 Analogs", *Chem. Biol. Interact.*, vol. 67, No. 3–4, pp. 199–213, 1988.

Li et al., "Adozelesin, a Selected Lead Among Cyclopropylpyrroloindole Analogs of the DNA–Binding Antibiotic, CC–1065", *Invest. New Drugs*, vol. 9, No. 2, pp. 137–148, 1991.

Ennis et al., "The EGF Receptor System as a Target for Antitumor Therapy", *Cancer Invest.*, vol. 9, No. 5, pp. 553–562, 1991.

Gutowski et al., "Epidermal Growth Factor Receptor–reactive Monoclonal Antibodies: Xenograft Antitumor Activity Alone and as Drug Immunoconjugates", *Cancer Res.*, vol. 51, No. 20, pp. 5471–5475, 1991.

Pardridge et al., "Selective Transport of an Anti–transferrin Receptor Antibody Through the Blood–brain barrier in vivo", *J. Pharmacol. Exp. Ther.*, vol. 259, No. 1, pp. 66–70, 1991.

Boger, D.L. et al.: J. Org. Chem., vol. 55, 1990, pp. 5823–5833.

Boger, D.L. et al.: Biorg. Med. Chem. Lett., vol. 1, 1991, pp. 115–120.

Organic Chemistry, 3rd ed., p. 727.

Hack's Chemical Dictionary, 4th ed., 9. 35.

1

2

3

SCHEME 2a

SCHEME 2b

SCHEME 2c

METHOD A

METHOD B

TARGETED DELIVERY OF CYCLOPROPYLBENZINDOLE-CONTAINING CYTOTOXIC DRUGS

This is a continuation of application Ser. No. 08/210,742 filed Mar. 21, 1994, now U.S. Pat. No. 5,475,092 which is a continuation of Ser. No. 07/857,171, filed Mar. 25, 1992, now abandoned.

FIELD OF THE INVENTION

The present invention relates to novel cytotoxic agents and their therapeutic use. More specifically, the invention relates to novel cytotoxic agents comprising analogues of CC-1065 and derivatives of CC-1065 and their therapeutic use. These novel cytotoxic agents have therapeutic use as a result of delivering the analogues and derivatives to a specific cell population in a targeted fashion by chemically linking the analogues and derivatives to a cell binding agent.

BACKGROUND OF THE INVENTION

In recent years, a myriad of reports have appeared on the attempted specific targeting of tumor cells with monoclonal antibody-drug conjugates {(Sela et al, in *Immunoconjugates*, pp. 189–216 (C. Vogel, ed. 1987); Ghose et al, in *Targeted Drugs*, pp. 1–22 (E. Goldberg, ed. 1983); Diener et al, in *Antibody Mediated Delivery Systems*, pp. 1–23 (J. Rodwell, ed. 1988); Pietersz et al, in *Antibody Mediated Delivery Systems*, pp. 25–53 (J. Rodwell, ed. 1988); Bumol et al, in *Antibody Mediated Delivery Systems*, pp. 55–79 (J. Rodwell, ed. 1988)}. Cytotoxic drugs such as methotrexate, daunorubicin, doxorubicin, vincristine, vinblastine, melphalan, mitomycin C, chlorambucil, and maytansinoids have been conjugated to a variety of murine monoclonal antibodies. In some cases, the drug molecules were linked to the antibody molecules through an intermediary carrier molecule such as serum albumin {Garnett et al, 46 *Cancer Res.* 2407–2412 (1986); Ohkawa et al, 23 *Cancer Immunol. Immunother.* 81–86 (1986); Endo et al, 47 *Cancer Res.* 1076–1080 (1980)}, dextran {Hurwitz et al, 2 *Appl. Biochem.* 25–35 (1980); Manabi et al, 34 *Biochem. Pharmacol.* 289–291 (1985); Dillman et al, 46 *Cancer Res.* 4886–4891 (1986); Shoval et al, 85 *Proc. Natl. Acad. Sci. U.S.A.* 8276–8280 (1988)}, or polyglutamic acid {Tsukada et al, 73 *J. Natl. Canc. Inst.* 721–729 (1984); Kato et al, 27 *J. Med. Chem.* 1602–1607 (1984); Tsukada et al, 52 *Br. J. Cancer* 111–116 (1985)}.

A wide array of linker technologies have been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers {102 *Biochem. Biophys. Res. Commun.* 1048–1054 (1981)}. Yang and Reisfeld used the same technique to conjugate daunorubicin to an anti-melanoma antibody {80 *J. Natl. Canc. Inst.* 1154–1159 (1988)}. Dillman et al also used an acid-labile linker in a similar fashion to prepare conjugates of daunorubicin with an anti-T cell antibody {48 *Cancer Res.* 6097–6102 (1988)}.

An alternative approach, explored by Trouet et al, involved linking daunorubicin to an antibody via a peptide spacer arm {79 *Proc. Natl. Acad. Sci. U.S.A.* 626–629 (1982)}. This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al, 260 *J. Biol. Chem.* 12035–12041 (1985); Lambert et al, in *Immunotoxins* 175–209 (A. Frankel, ed. 1988); Ghetie et al, 48 *Cancer Res.* 2610–2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al described the conversion of methotrexate into a mercaptoethylamide derivative followed by conjugation with poly-D-lysine via a disulfide bond {260 *J. Biol. Chem.* 10905–10908 (1985)}. A recent report described the preparation of a conjugate of the trisulfide containing toxic drug calicheamycin with an antibody {Menendez et al, *Fourth International Conference on Monoclonal Antibody Immunoconjugates for Cancer*, San Diego, Abstract 81 (1989)}.

One reason for the lack of disulfide linked antibody-drug conjugates is the unavailability of cytotoxic drugs possessing a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin and vincristine. In order to achieve significant cytotoxicity, linkage of a large number of drug molecules either directly to the antibody or through a polymeric carrier molecule becomes necessary. However such heavily modified antibodies often display impaired binding to the target antigen and fast in vivo clearance from the blood stream.

CC-1065 is a potent antitumor-antibiotic isolated from cultures of *Streptomyces zelensis* and has been shown to be exceptionally cytotoxic in vitro.

The structure of CC-1065 (Compound 1, FIG. 1A) has been determined by X-ray crystallography {Martin, D. G. et al, 33 *J. Antibiotics* 902–903 (1980), and Chidester, C. G., et al, 103 *J. Am. Chem. Soc.* 7629–7635 (1981)}. The CC-1065 molecule consists of 3 substituted pyrroloindole moieties linked by amide bonds. The "A" subunit has a cyclopropyl ring containing the only asymmetric carbons in the molecule. While only the relative configuration of these carbons is available from X-ray data, the absolute configuration has been inferred as 3bR, 4aS by using DNA as a chiral reagent {Hurley, L. H. et al, 226 *Science* 843–844 (1984)}. The "B" and "C" subunits are identical pyrroloindole moieties.

The cytotoxic potency of CC-1065 has been correlated with the alkylating activity and the DNA-binding or DNA-intercalating activity of CC-1065. The two activities reside in two separate parts of the molecule. The alkylating activity is contained in the CPI unit A (cpclopropapyrroloindole unit) and the DNA-binding in the two subunits B and C (see FIG. 1A).

CC-1065 is 100 to 1000-fold more cytotoxic than conventional cancer chemotherapeutic agents such as methotrexate, daunorubicin and vincristine {B. K. Bhuyan et al, 42 *Cancer Res.* 3532–3537 (1982)}. However, administration of CC-1065 to mice causes a delayed hepatotoxicity leading to death at 50 days after a single i.v. dose of 12.5 μg/kg {V. L. Reynolds et al, XXXIX *J. Antibiotics* 319–334 (1986)}. The synthesis of some new analogues of CC-1065 (FIGS. 1B and 1C) that retain the high in vitro cytotoxicity of the parent drug without causing delayed lethality in mice have been reported recently {M. A. Warpehoski et al, 31 *J. Med. Chem.* 590–603 (1988)}. Like CC-1065, these analogues are alkylating agents that bind to DNA in a covalent manner causing cell death. These compounds inhibit the growth of L1210 murine leukemia cells in vitro with $IC_{50}$ values in the range of $1\times10^{-10}$ to $1\times10^{-11}$M. Some of these compounds display in vivo efficacy against P388 leukemia in mice. The most effective analogue U-73975 (FIG. 1C) shows a 170% increase in life span over untreated controls at the optimal dose of 0.05 mg/kg given i.p. on days 1, 5, and 9. However, at this dose, only 1 out of 6 treated mice survived beyond 30 days. Therefore, these drugs have very little therapeutic value because of their high toxicity at concentrations necessary for therapeutic effects.

Accordingly, a need exists to improve the therapeutic efficacy of CC-1065 and its analogues such that the compounds retain cytotoxic activity but have decreased systemic toxicity.

SUMMARY OF THE INVENTION

The object of the present invention is to provide analogues and derivatives of CC-1065 which are capable of being covalently linked to a cell binding agent. The cell binding agent conjugates allow targeted delivery of the analogues and derivatives without substantially interfering with their cytotoxic activity, thereby lowering toxicity to non-targeted cells and hence, lowering systemic toxicity.

This and other objects have been achieved by providing a cytotoxic agent comprising a cell binding agent linked to one or more analogues and derivatives of CC-1065, wherein prior to linking the analogues and derivatives to the cell binding agent the analogues and derivatives are selected from the group consisting of an A subunit of the formulae (A-1), (A-2), (A-3), or (A-4) covalently linked to a B subunit or a B-C subunit of the formulae (F-1), (F-2), (F-3), (F-4), (F-5), (F-6), (F-7), (F-8), (F-9) or (F-10) via an amide bond from the secondary amino group of the pyrrole moiety of the A subunit to the C-2 carboxyl group of the B subunit, wherein the formulae A-1 to A-4 are as follows:

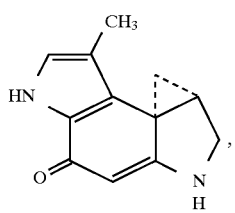
(A-1)

-continued

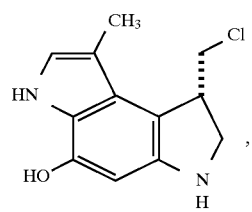
(A-2)

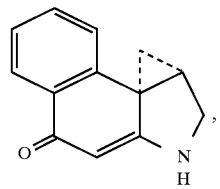
(A-3)

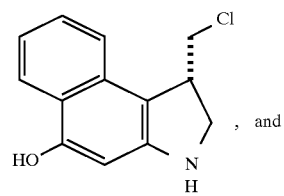
(A-4)

, and wherein the formulae (F-1) to (F-10) are as follows:

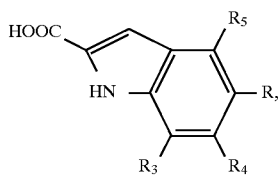
(F-1)

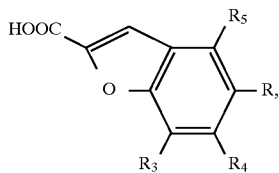
(F-2)

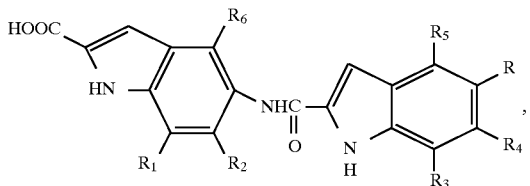
(F-3)

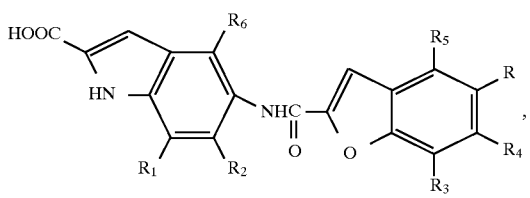
(F-4)

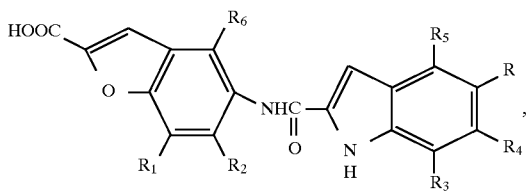
(F-5)

-continued

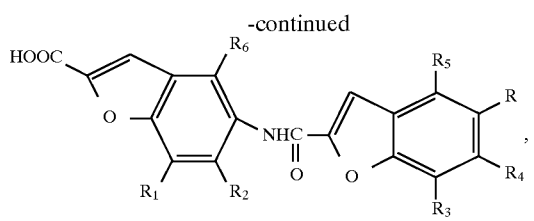 (F-6)

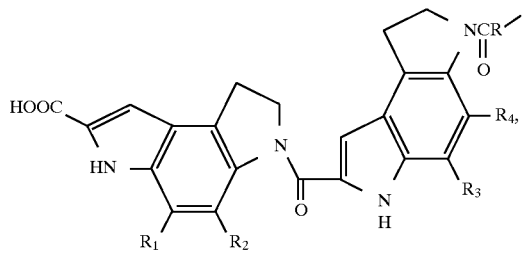 (F-7)

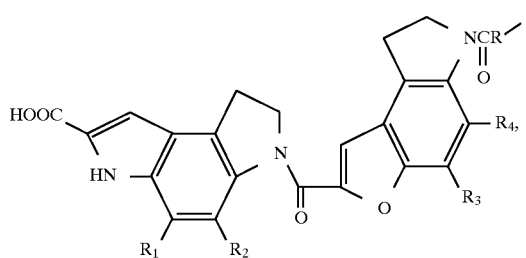 (F-8)

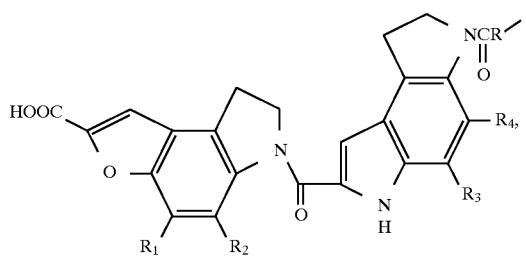 (F-9)

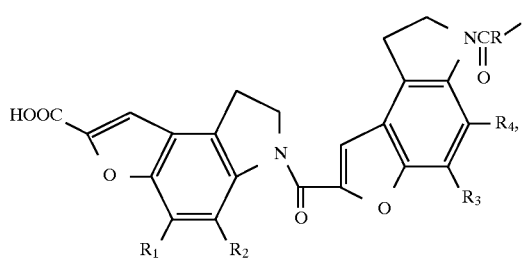 (F-10)

wherein in a given formula, one of either R and R' or $R_4$ represents a moiety that enables linkage of the analogue or derivative of CC-1065 to a cell binding agent; when R or R' represent moieties that enable linkage, then $R^1$ to $R_6$, which may be the same or different, represent hydrogen, $C_1$–$C_3$ linear alkyl, methoxy, hydroxyl, primary amino, secondary amino, tertiary amino, or amido; and when $R_4$ represents a moiety that enables linkage, R, $R_1$, $R_2$, $R_3$, $R^5$ and $R_6$, which may be the same or different, represent hydrogen, $C_1$–$C_3$ linear alkyl, methoxy, hydroxyl, primary amino, secondary amino, tertiary amino, or amido, and R' represents $NH_2$, alkyl, O-alkyl, primary amino, secondary amino, tertiary, or amido.

The present invention also provides a therapeutic agent for killing selected cell populations comprising:

(a) a cytotoxic amount of one or more of the above-described cytotoxic agents, and
(b) a pharmaceutically acceptable carrier, diluent, or excipient.

A further object of the present invention is to provide the method for killing selected cell populations comprising contacting a cell population or tissue suspected of containing cells from the selected cell population with a cytotoxic amount of one or more of the above-described cytotoxic agents.

An even further object of the present invention is to provide an analogue or derivative of CC-1065 selected from the group consisting of an A subunit of the formulae (A-1), (A-2), (A-3), or (A-4) covalently linked to a B subunit or a B-C subunit of the formulae (F-1), (F-2), (F-3), (F-4), (F-5), (F-6), (F-7), (F-8), (F-9) or (F-10) via an amide bond from the secondary amino group of the pyrrole moiety of the A subunit to the C-2 carboxyl group of the B subunit, wherein the formulae A-1 to A-4 are as follows:

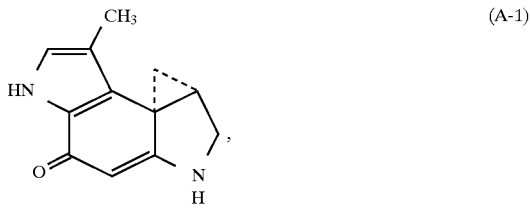 (A-1)

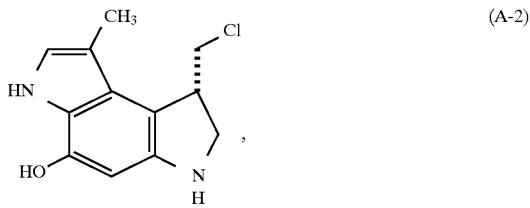 (A-2)

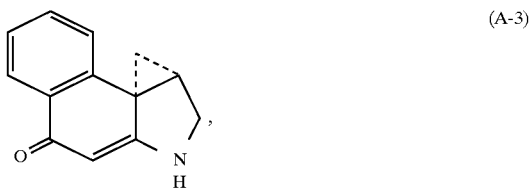 (A-3)

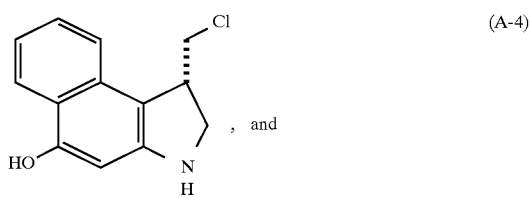 (A-4)

wherein the formulae (F-1) to (F-10) are as follows:

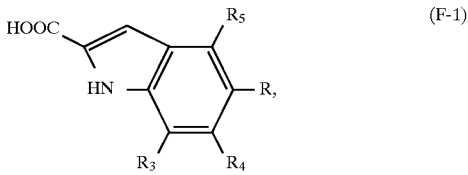 (F-1)

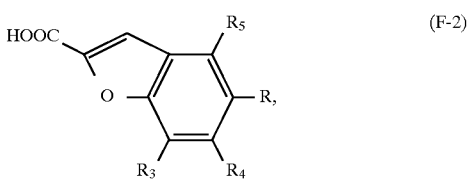 (F-2)

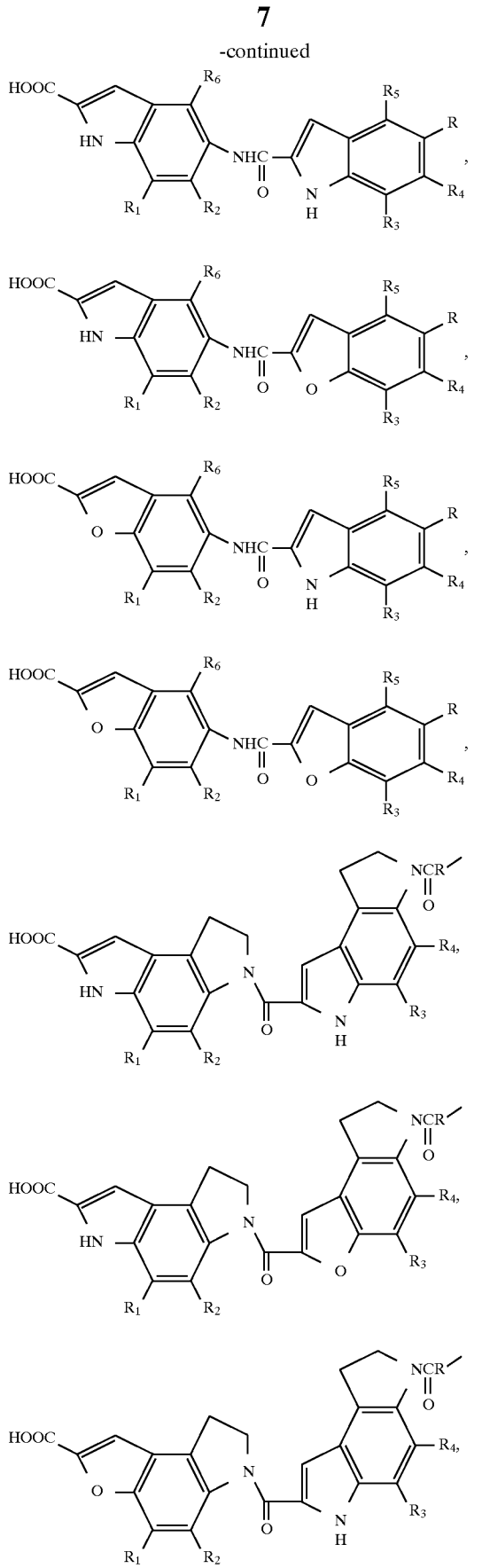

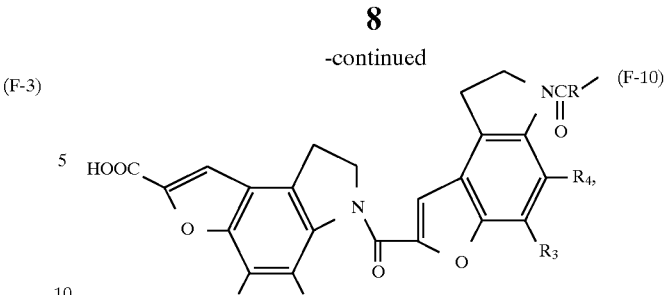

wherein in a given formula, one of either R and R' or $R_4$ represents a moiety that enables linkage of the analogue or derivative of CC-1065 to a cell binding agent; when R or R' represent moieties that enable linkage, then $R_1$ to $R_6$, which may be the same or different, represent hydrogen, $C_1$–$C_3$ linear alkyl, methoxy, hydroxyl, primary amino, secondary amino, tertiary amino, or amido; and when $R_4$ represents a moiety that enables linkage, R, $R_1$, $R_2$, $R_3$, $R_5$ and $R_6$, which may be the same or different, represent hydrogen, $C_1$–$C_3$ linear alkyl, methoxy, hydroxyl, primary amino, secondary amino, tertiary amino, or amido, and R' represents $NH_2$, alkyl, O-alkyl, primary amino, secondary amine, tertiary amine, or amido.

BRIEF DESCRIPTION OF THE DRAWINGS

FIG. 5A is a diagram of a method using a thiol-containing CC-1065 analogue and FIG. 5B is a diagram of a method using an activated disulfide-containing CC-1065 analogue.

Figure 9:
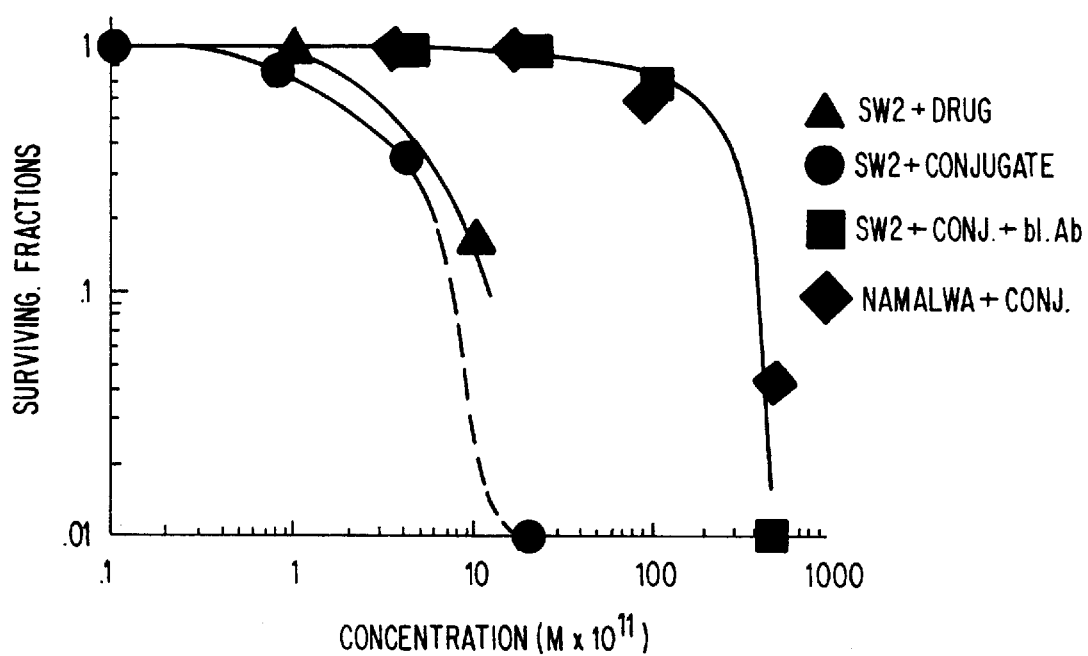

FIG. 9 is a graph showing in vitro cytotoxicity and specificity of the CC-1065 analogue 22 conjugate of the present invention toward SW2 and Namalwa cells. The abscissa represents the concentration of conjugate or free CC-1065 analogue 22, and the ordinate represents the surviving fraction of cells. The circles represent data for the conjugate for the antigen positive SW2 cells, the triangles represent data for free CC-1065 analogue 22, the squares represent data for conjugate in the presence of free antibody, and the diamonds represent data for the conjugate for the antigen negative Namalwa cells.

DETAILED DESCRIPTION OF THE INVENTION

Figure 1A:
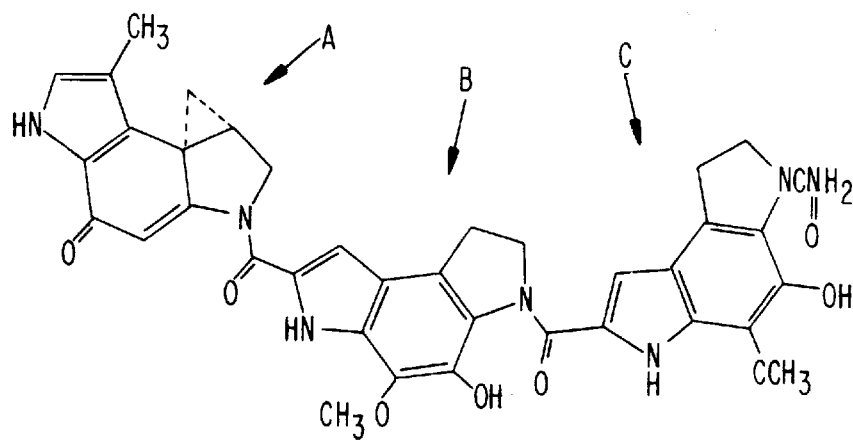
FIG. 1A shows the structure of CC-1065 and its subunits A, B, and C.
Figure 1B:
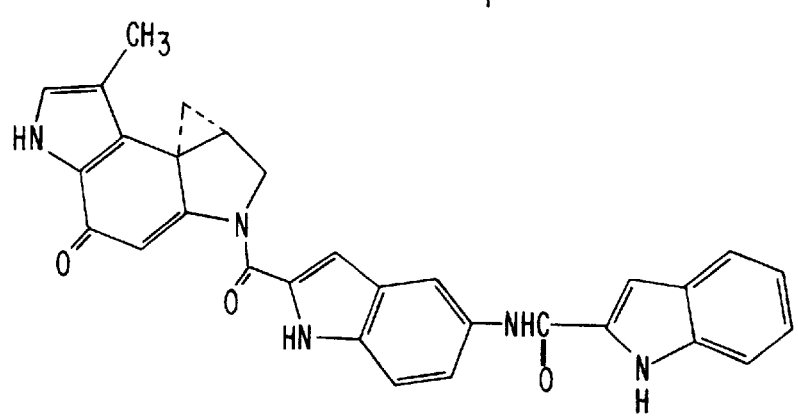
FIG. 1B and FIG. 1C show the structures of two known analogues of CC-1065.

The present inventors have found that the therapeutic efficacy of CC-1065 and analogues thereof can be improved by changing the in vivo distribution through targeted delivery of the drug to the tumor site resulting in a lower toxicity to non-targeted tissues, and hence lower systemic toxicity. In order to achieve this goal, the inventors synthesized analogues of the cytotoxic drugs 2 and 3 (FIGS. 1B and 1C) that contain a thiol or disulfide group containing substituent at the C-5 position of the terminal indolyl or benzofuranyl moiety of the drug. These compounds not only retain the high cytotoxicity of the parent drug but can also be linked to cell binding agents via disulfide bonds. The inventors have previously shown that the linkage of highly cytotoxic drugs to antibodies using a cleavable link, such as a disulfide bond, ensures the release of fully active drug inside the cell, and such conjugates are cytotoxic in an antigen specific manner {R. V. J. Chari et al, 52 *Cancer Res.* 127–131 (1992); U.S. Pat. No. 5,208,020}. In the present application, the inventors describe the synthesis of new drug analogues, procedures for their conjugation to monoclonal antibodies and in vitro cytotoxicity and specificity of these conjugates. This invention permits the analogues and derivatives of CC-1065 to live up to their potential, something their undirected cytotoxic effects had previously made impossible. Thus the invention provides useful agents for the elimination of diseased or abnormal cells that are to be killed or lysed such as tumor cells, virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

Thus, this invention teaches the synthesis of analogues and derivatives of CC-1065 that can be chemically linked to a cell binding agent and that have maintained the high cytotoxicity of the parent compound CC-1065. Further, these compounds when linked to a cell binding agent are only highly cytotoxic to cells to which the cell binding agent binds and much less toxic to nonspecific cells. High cytotoxicity is defined as having an $IC_{50}$ of about $10^{-9}M$ or less when measured in vitro with SW2 cells upon a 24 hour exposure time to the drug. The parent compound shows under these conditions an $IC_{50}$ of $2\times10^{-10}M$.

Cytotoxic Agent

The cytotoxic agent according to the present invention comprises one or more analogues or derivatives of CC-1065 linked to a cell binding agent.

According to the present invention, the analogues and derivatives of CC-1065 must contain an A subunit CPI (cyclopropapyrroloindole unit) in its natural closed cyclopropyl form or in its open chloromethyl form, or the closely related CBI unit (cyclopropylbenzindole unit) in the closed cyclopropyl form or the open chloromethyl form. The B and C subunits of CC-1065 are very similar and are 2-carboxy-indole derivatives. The analogues of CC-1065 need for activity at least one such 2-carboxy-indole subunit or a 2-carboxy-benzofuran subunit, although two subunits (i.e., B and C) render the analogue more potent. As is obvious from the natural CC-1065 and from the analogues published {e.g. Warpehoski et al, 31 *J. Med. Chem.* 590–603 (1988)}, the B and C subunits can also carry different substituents at different positions on the indole or benzofuran rings.

In order to link CC-1065 to a cell binding agent, the CC-1065 must first be derivatized to include a moiety that allows the derivatives to be linked to a cell binding agent via a disulfide bond, an acid-labile group, a photo-labile group, a peptidase-labile group, or an esterase-labile group. The analogues are prepared so that they already contain a moiety necessary to link the analogue to a cell binding agent via a disulfide bond, an acid-labile group, a photo-labile group, a peptidase-labile group, or an esterase-labile group.

More specifically, according to the present invention, analogues or derivatives of CC-1065 can be any of the following A subunits of the formulae (A-1){CPI (Cyclopropyl form)}, (A-2){CPI (Chloromethyl form)}, (A-3){CBI (Cyclopropyl form)}, and (A-4){CBI (Chloromethyl form)} covalently linked via an amide bond from the secondary amino group of the pyrrole moiety of the A subunit to the C-2 carboxy group of the following B or covalently bound B and C subunits having the formulae (F-1) to (F-10).

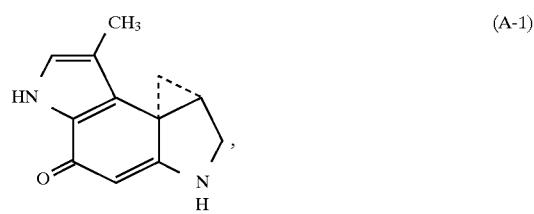

(A-1)

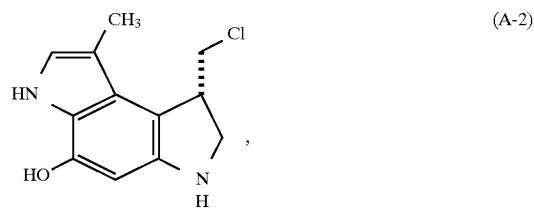

(A-2)

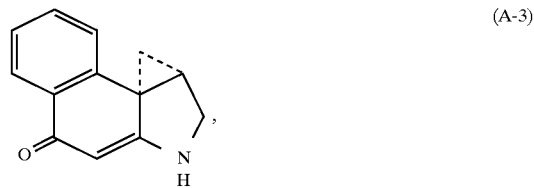

(A-3)

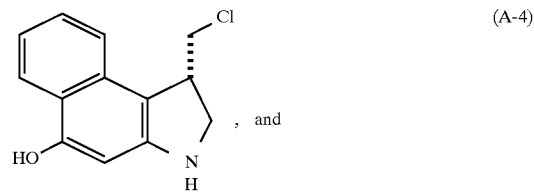

, and (A-4)

B and Covalently Bound B and C Subunits

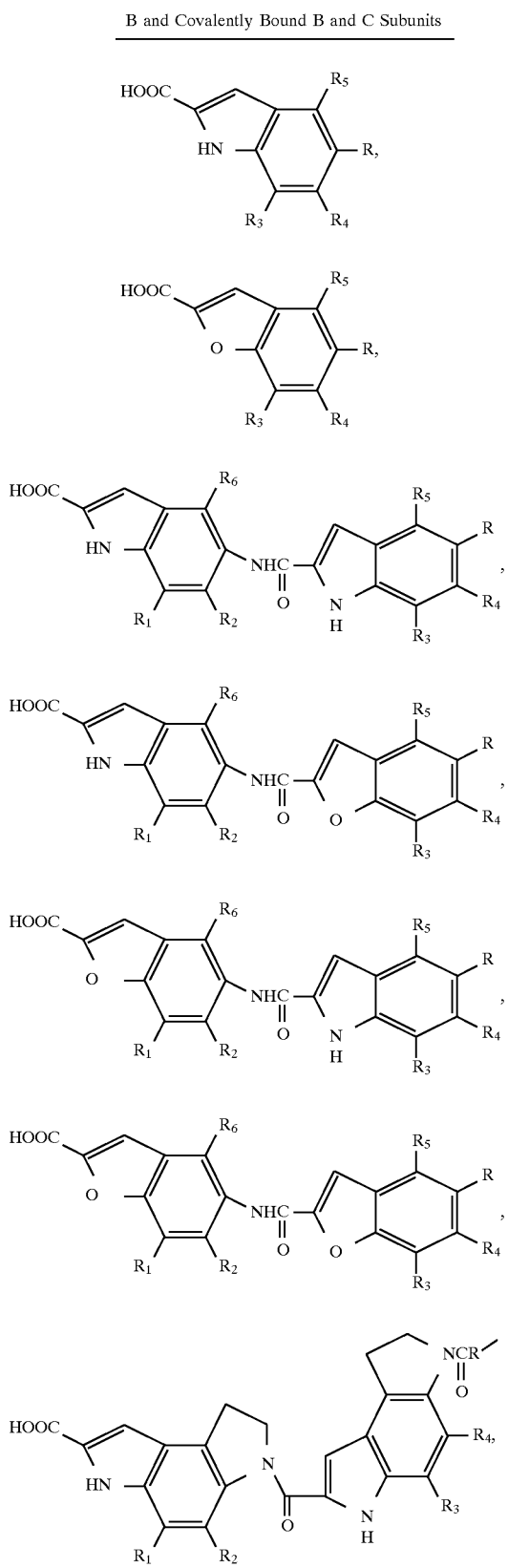

B and Covalently Bound B and C Subunits -continued

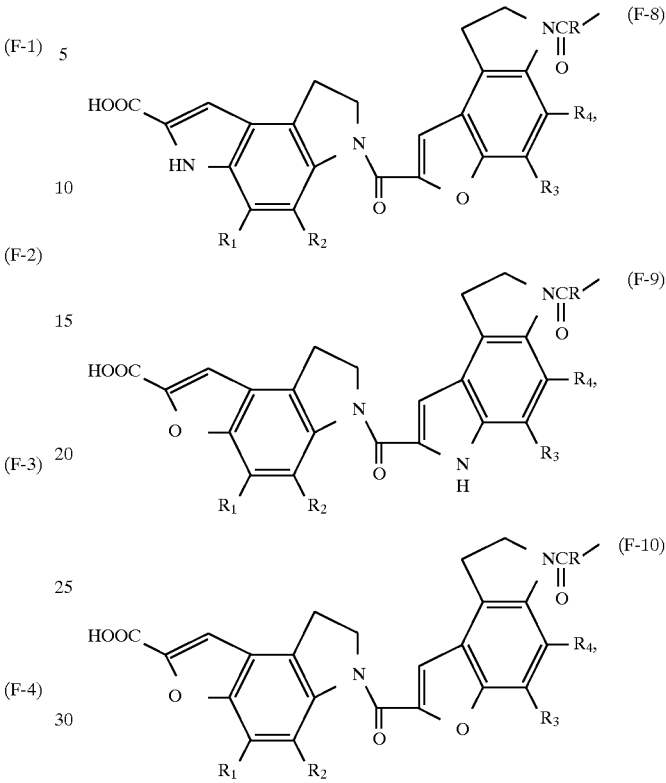

wherein in a given formula, one of either R and R' or $R_4$ represents a moiety that enables linkage of the analogue or derivative of CC-1065 to a cell binding agent; when R or R' represent moieties that enable linkage, then $R_1$ to $R_6$, which may be the same or different, represent hydrogen, $C_1$–$C_3$ linear alkyl, methoxy, hydroxyl, primary amino, secondary amino, tertiary amino, or amido; and when $R_4$ represents a moiety that enables linkage, R, $R_1$, $R_2$, $R_3$, $R_5$ and $R_6$, which may be the same or different, represent hydrogen, $C_1$–$C_3$ linear alkyl, methoxy, hydroxyl, primary amino, secondary amino, tertiary amino, or amido, and R' represents $NH_2$, alkyl, O-alkyl, primary amino, secondary amino, tertiary amino, or amido.

Examples of primary amino group-containing substituents are methyl amino, ethyl amino, and isopropyl amino.

Examples of secondary amino group-containing substituents are dimethyl amino, diethyl amino, and ethyl-propyl amino.

Examples of tertiary amino group-containing substituents are trimethyl amino, triethyl amino, and ethyl-isopropyl-methyl amino.

Examples of amido groups include N-methyl-acetamido, N-methyl-propionamido, N-acetamido, and N-propionamido.

Examples of alkyl represented by R', when R' is not a linking group, include $C_1$–$C_5$ linear or branched alkyl.

Examples of O-alkyl represented by R', when R' is not a linking group, include compounds where the alkyl moiety is a $C_1$–$C_5$ linear or branched alkyl.

In a preferred embodiment, $R_1$ to $R_6$ are all hydrogen, and R and R' represent moieties that enable linkage of the derivative of CC-1065 or the derivative of the analogue of CC-1065 to a cell binding agent via a disulfide bond.

In an especially preferred embodiment, R or $R_4$ represent $NHCO(CH_2)_lSZ_0$, $NHCOC_6H_4(CH_2)_lSZ_0$, or $O(CH_2)_lSZ_0$ and R' represents $(CH_2)_lSZ_0$, $NH(CH_2)_lSZ_0$ or $O(CH_2)_lSZ_0$, wherein: $Z_0$ represents H or $SR_7$, wherein $R_7$ represents methyl, linear alkyl, branched alkyl, cyclic alkyl, simple or substituted aryl or heterocyclic, and l represents an integer of 1 to 10.

Examples of linear alkyls represented by $R_7$ include methyl, ethyl, propyl, butyl, pentyl and hexyl.

Examples of branched alkyls represented by $R_7$ include isopropyl, isobutyl, sec.-butyl, tert.-butyl, isopentyl and 1-ethyl-propyl.

Examples of cyclic alkyls represented by $R_7$ include cyclopropyl, cyclobutyl, cyclopentyl and cyclohexyl.

Examples of simple aryls represented by $R_7$ include phenyl and naphthyl.

Examples of substituted aryls represented by $R_7$ include aryls such as phenyl or naphthyl substituted with alkyl groups, with halogens, such as Cl, Br, F, nitro groups, amino groups, sulfonic acid groups, carboxylic acid groups, hydroxy groups and alkoxy groups.

Heterocyclics represented by $R_7$ are compounds wherein the heteroatoms are selected from O, N, and S, and examples include furyl, pyrrollyl, pyridyl, (e.g., a 2-substituted pyrimidine group) and thiophene.

Disulfide-containing and mercapto-containing analogues and derivatives of CC-1065 of the invention can be evaluated for their ability to suppress proliferation of various unwanted cell lines in vitro. For example, cell lines such as the human epidermoid carcinoma line KB, the human breast tumor line SKBR3, and the Burkitt's lymphoma line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

The in vitro cytotoxicity towards human cancer cell lines of the mono-indolyl CC-1065 analogue 6, the indolyl-benzofuranyl-CPI compound 18 and the bis-indolyl CPI derivative 22 were determined. Thus the monoindolyl compound 6 had an $IC_{50}$ value between $2.0–7.0\times10^{-10}M$ towards the different cell lines tested (SW2, Namalwa and A-375). CPI derivative 18 was highly cytotoxic towards the human small cell lung cancer cell line SW2 and the human Burkitt's lymphoma cell line Namalwa with $IC_{50}$ values of $5\times10^{-12}M$ and $1\times10^{-11}M$, respectively, after a 24 h exposure to the drug. The bis-indolyl CPI derivative 22 was also very cytotoxic with an $IC_{50}$ value of $4\times10^{-11}M$ towards SW2 cells.

The above-described analogues and derivatives of CC-1065 can be prepared by known methods which may involve isolation from natural sources and subsequent modification, synthetic preparation, or a combination of both.

Representative synthesis examples are described below.

Synthesis Example 1

Figure 2:
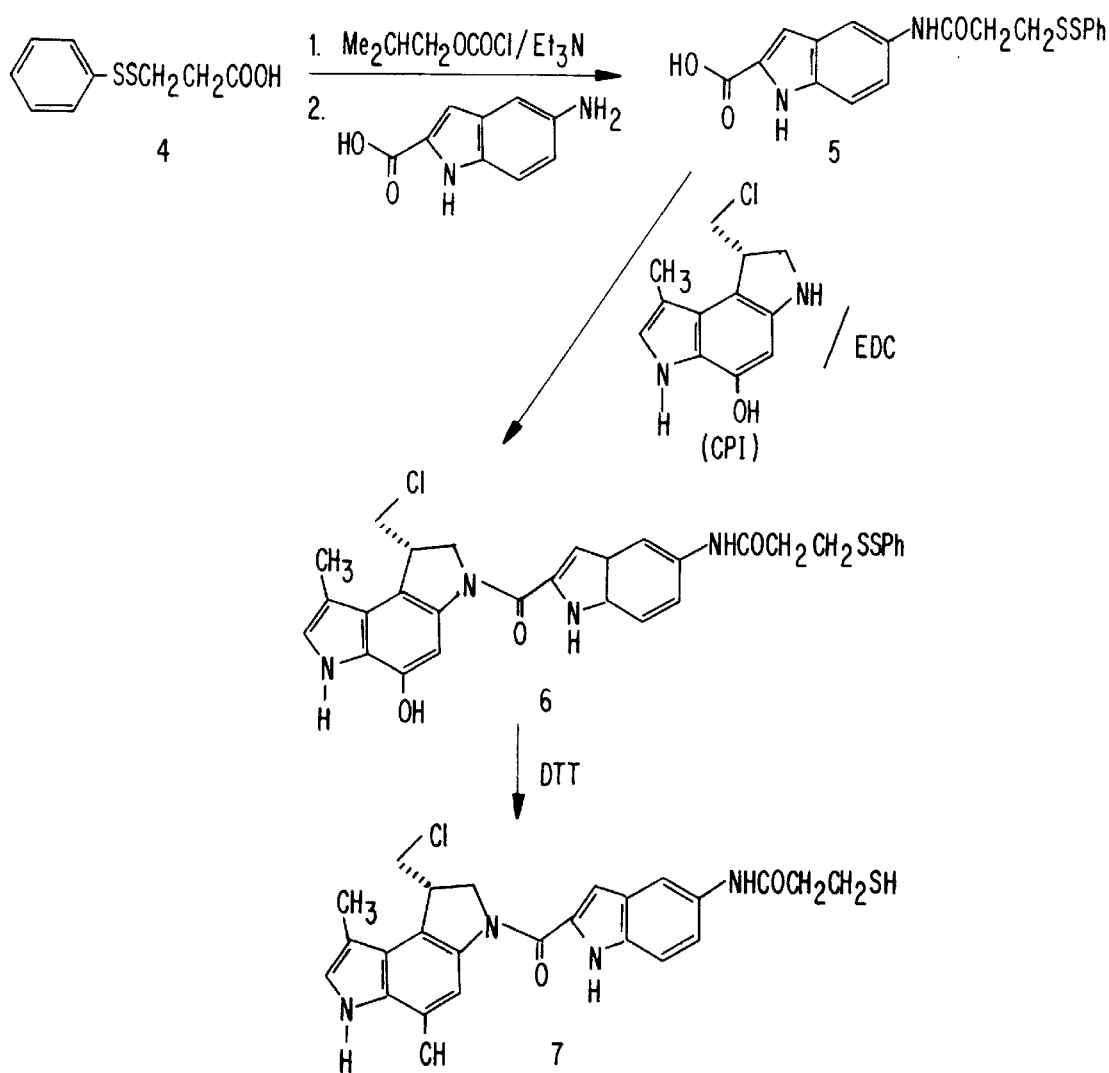
FIG. 2 is a synthesis scheme for preparing mono-indolyl CC-1065 analogue 7 of the present invention.

The synthesis of the mono-indolyl CC-1065 analogue 7 containing a thiol substituent on the side chain at C-5 of the indole moiety of the B subunit is outlined in Scheme 1 (FIG. 2). Phenyldithiopropionic acid 4 was treated with isobutylchloroformate in the presence of triethylamine to give the mixed anhydride followed by reaction with 5-aminoindole-2-carboxylic acid to give the amide 5. Coupling of 5 with CPI was carried out in the presence of ethyl-diaminopropyl-carbodiimide (EDC) as previously described {M. A. Warpehoski et al, 31 *J. Med. Chem.* 590–603 (1988)} to give the phenyldithio group containing CPI derivative 6. Reduction of 6 to the thiol-containing derivative 7 proceeded smoothly in the presence of 1.1 equivalents of dithiothreitol at 4° C. The reaction was judged to be complete in 1 h and the product was purified by HPLC using a reverse phase C-18 column.

Synthesis Example 2

Figure 3A:
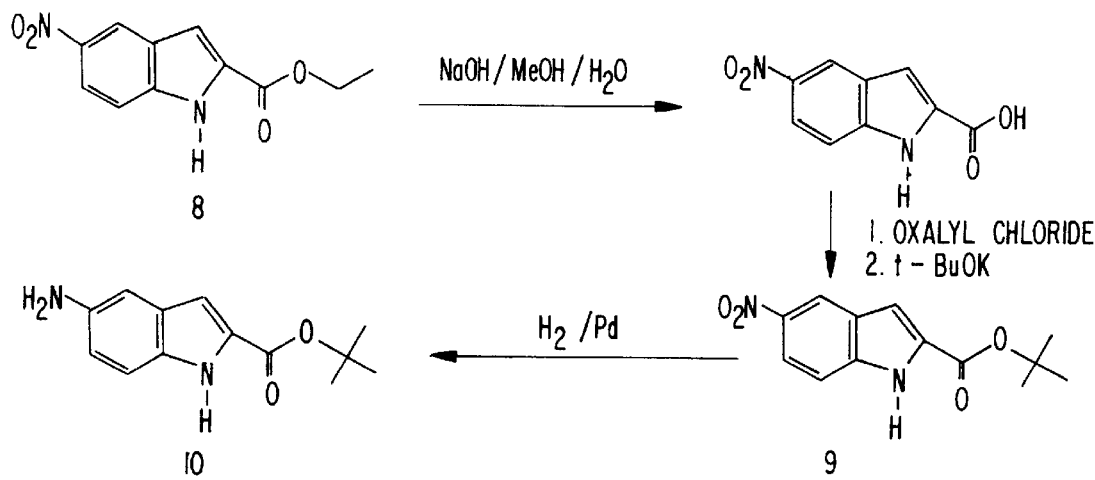
FIGS. 3A, 3B, and 3C are synthesis schemes for preparing indolyl-benzofuranyl CC-1065 analogue 18 of the present invention.
Figure 3B:
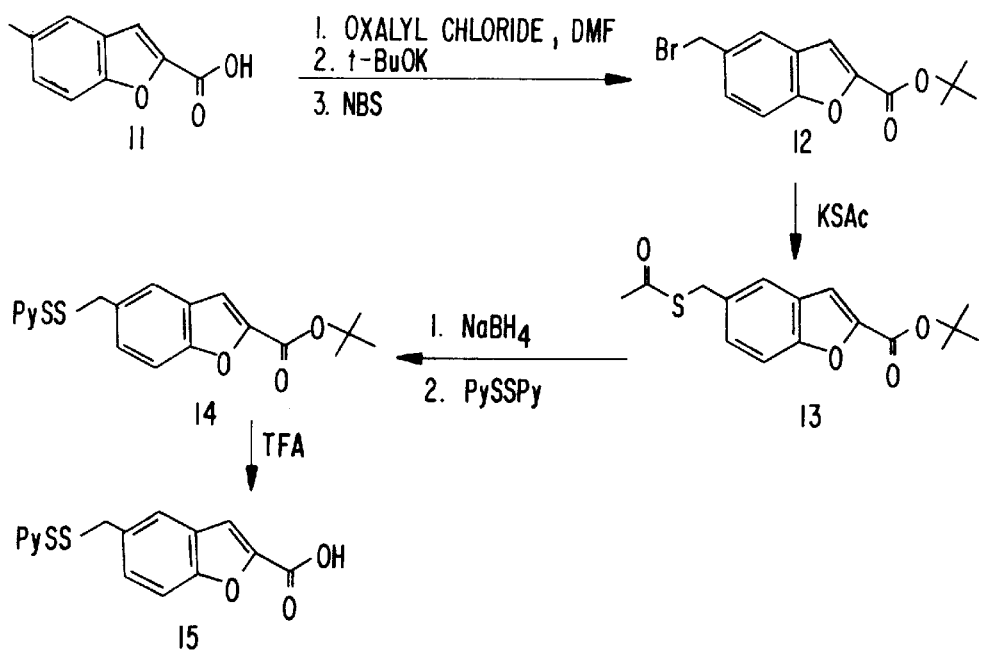
Figure 3C:
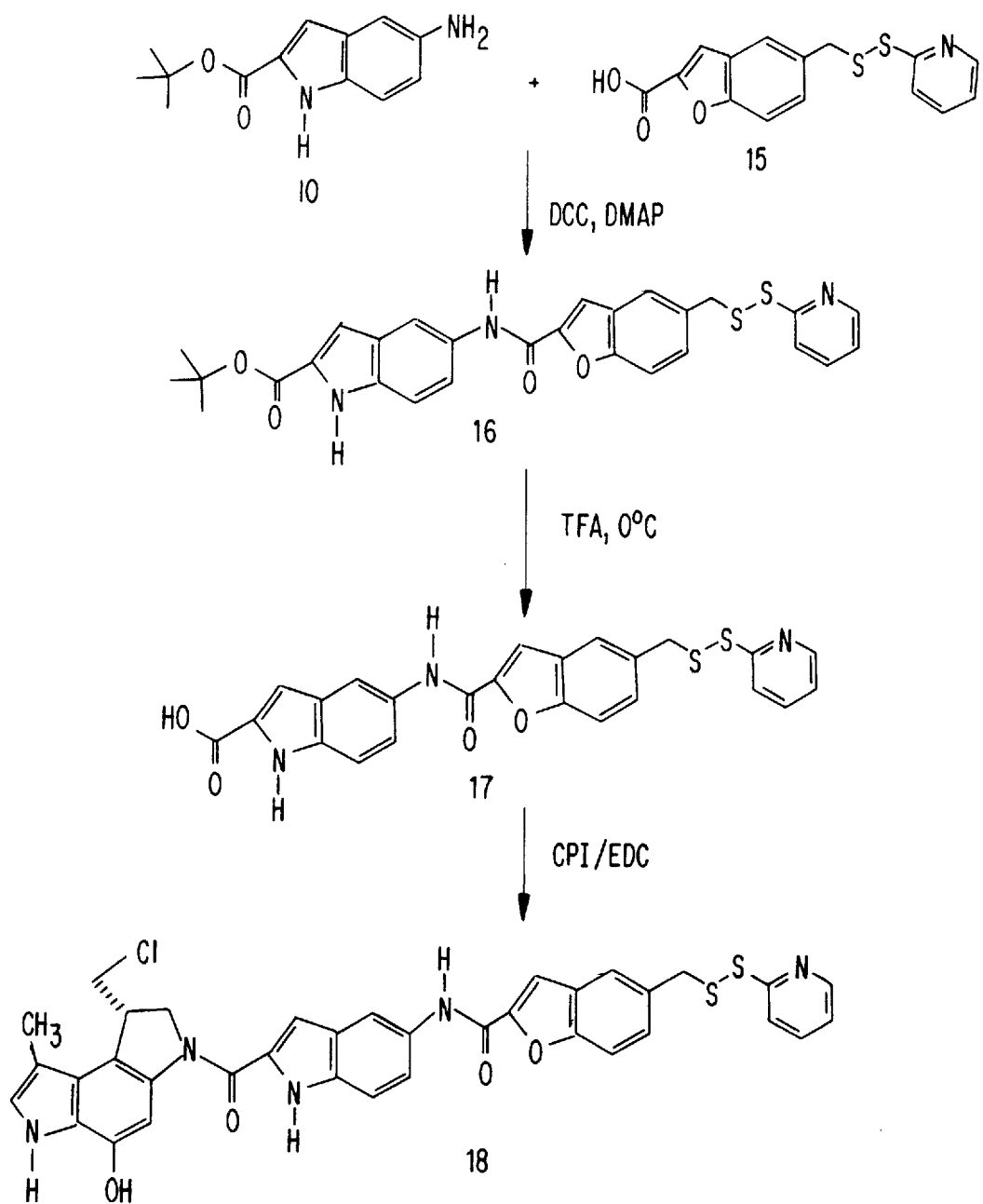

The synthetic steps of the preparation of the 0indolyl-benzofuranyl-CPI derivative 18 containing an activated disulfide group are outlined in Schemes 2 and 3 (FIGS. 3A, 3B, 3C and 4). tert-Butyl 5-aminoindole-2-carboxylate 10 was prepared from ethyl 5-nitroindole-2-carboxylate 8 (Scheme 2a; FIG. 3A). 5-(2'-Pyridyldithio-methyl)benzofuran-2-carboxylic acid 15 was prepared from 5-methylbenzofuran-2-carboxylic acid 11 (Scheme 2b; FIG. 3B). Carboxylic acid 11 was converted to its tert-butyl ester and then brominated at the benzylic position with N-bromosuccinimide (NBS) to give the mono-bromomethyl compound 12. Displacement of bromide with thioacetate, followed by reduction with sodium borohydride and reaction of the free thiol with 2-pyridyldisulfide gave ester 14. Hydrolysis of the tert-butyl ester with trifluoroacetic acid proceeded smoothly at 0° C. to give 15. Coupling of 15 with tert-butyl-5-aminoindole-2-carboxylate 10 was effected with dicyclohexylcarbodiimide/4-N,N-dimethylaminopyridine (DCC/DMAP) or carbonyldiimadazole to give the indolyl-benzofuranyl compound 16. Hydrolysis of the tert-butyl ester to give the carboxylic acid 17, followed by coupling with CPI in the presence of EDC gave the drug 18 (Scheme 2c; FIG. 3C).

Synthesis Example 3

Figure 4:
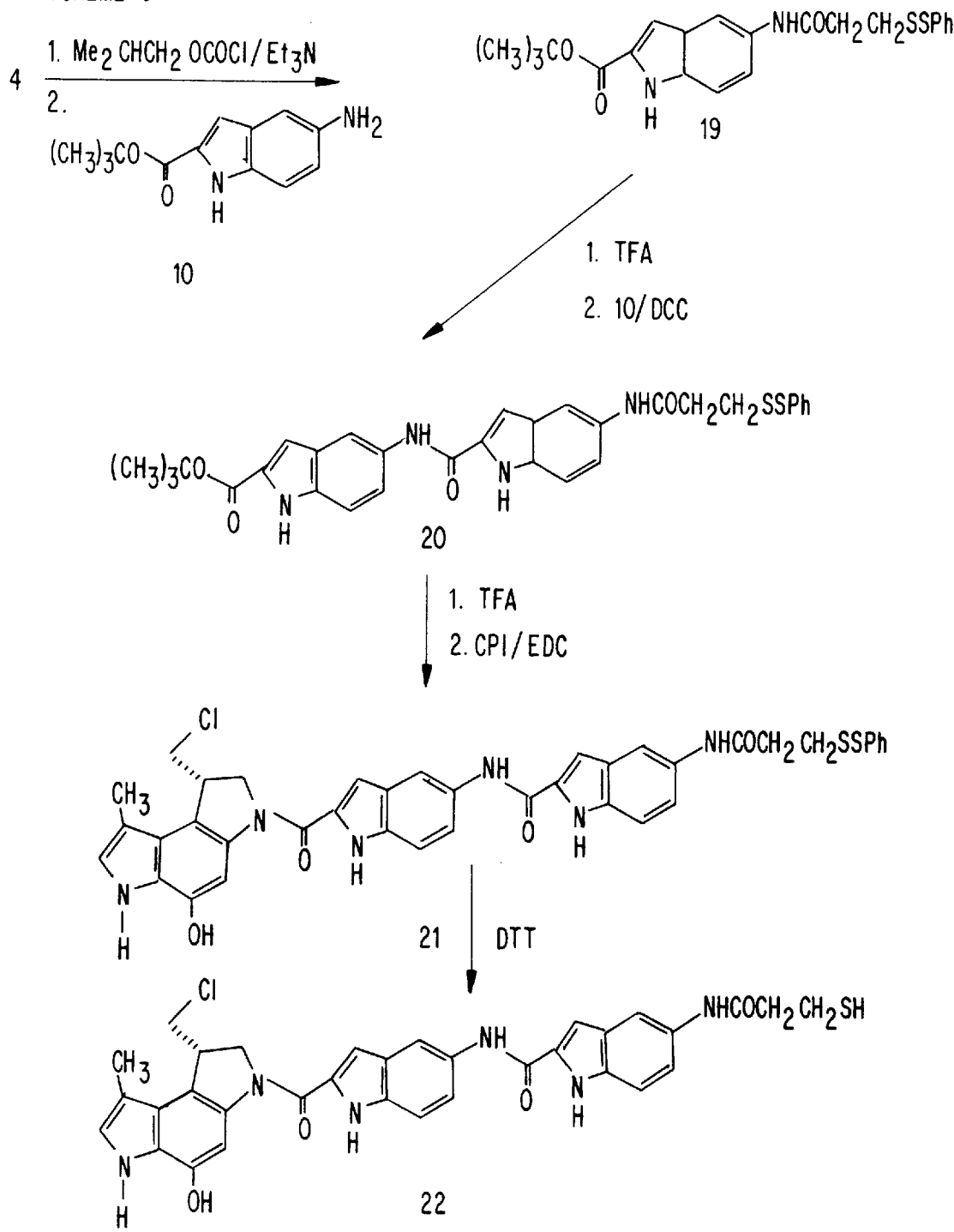
FIG. 4 is a synthesis scheme for preparing bis-indolyl CC-1065 analogue 22 of the present invention.

The thiol-containing bis-indolyl-CPI derivative 22 was synthesized by the steps outlined in Scheme 3 (FIG. 4). Phenyldithiopropionic acid 4 was activated with isobutyl-chloroformate and then reacted with tert-butyl 5-aminoindole-2-carboxylate 10 to give ester 19. Hydrolysis of the tert-butyl ester with trifluoroacetic acid, followed by coupling with another molecule of 10 in the presence of DCC gave the bis-indolyl ester 20. Again, hydrolysis of ester 20 followed by coupling with CPI gave the drug 21. Cleavage of the phenyldithio protecting group with dithiothreitol at 0° C. under conditions identical to that used earlier for the reduction of the disulfide group in the mono-indolyl-CPI compound 6 afforded the thiol-containing drug 22.

Linking Groups

Linking groups other than those described above in the synthesis examples can also be used to prepare the derivatives of CC-1065 or the analogues of CC-1065 according to the present invention.

Suitable linking groups are well known in the art and include disulfide groups, thioether groups, acid-labile groups, photo-labile groups, peptidase-labile groups and esterase-labile groups. Preferred are disulfide groups.

According to the present invention the linking group is part of a chemical moiety that is covalently bound to CC-1065 or the CC-1065 analogue through conventional methods as described above. The chemical moiety can be covalently bound to the CC-1065 or CC-1065 analogue through an alkyl group, amino group, an amide bond or an ether bond at the C-4 or C-5 position of the terminal indole or benzofuran moiety. In a preferred embodiment, the chemical moiety can be covalently bound to the CC-1065 or CC-1065 analog via a methylene ($CH_2$) group or an amide group ($NHCOCH_2CH_2$) at the C-5 position of the terminal indole or benzofuran moiety.

Preparation of Cell Binding Agents

The effectiveness of the compounds of the invention as therapeutic agents depends on the careful selection of an appropriate cell binding agent. Cell binding agents may be of any kind presently known, or that become known and include peptides and non-peptides. Generally, these can be antibodies (especially monoclonal antibodies) or at least one binding site of an antibody, lymphokines, hormones, growth factors, nutrient-transport molecules (such as transferrin), or any other cell binding molecule or substance.

More specific examples of cell binding agents that can be used include:

monoclonal antibodies;
  single chain antibodies;
  fragments of antibodies such as Fab, Fab', F(ab')$_2$ and F$_v$ {Parham, 131 *J. Immunol.* 2895–2902 (1983); Spring et al, 113 *J. Immunol.* 470–478 (1974); Nisonoff et al, 89 *Arch. Biochem. Biophys.* 230–244 (1960)};
  interferons (e.g. $\alpha$, $\beta$, $\gamma$);
  lymphokines such as IL-2, IL-3, IL-4, IL-6;
  hormones such as insulin, TRH (thyrotropin releasing hormones), MSH (melanocyte-stimulating hormone), steroid hormones, such as androgens and estrogens;
  growth factors and colony-stimulating factors such as EGF, TGF-$\alpha$, G-CSF, M-CSF and GM-CSF {Burgess, 5 *Immunology Today* 155–158 (1984)}; and
  transferrin {O'Keefe et al, 260 *J. Biol. Chem.* 932–937 (1985)}.

Monoclonal antibody techniques allow for the production of extremely specific cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins.

Selection of the appropriate cell binding agent is a matter of choice that depends upon the particular cell population that is to be targeted, but in general monoclonal antibodies are preferred if an appropriate one is available.

For example, the monoclonal antibody J5 is a murine IgG$_{2a}$ antibody that binds specifically to the Common Acute Lymphoblastic Leukemia Antigen (CALLA) {Ritz et al, 283 *Nature* 583–585 (1980)} and can be used if the target cells express CALLA such as in the disease of acute lymphoblastic leukemia. Similarly, the monoclonal antibody anti-B4 is a murine IgG$_1$, that binds to the CD19 antigen on B cells {Nadler et al, 131 *J. Immunol.* 244–250 (1983)} and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH which binds to melanocytes can be used for the treatment of melanoma.

Cancers of the breast and testes can be successfully targeted with estrogen (or estrogen analogues) or androgen (or androgen analogues) respectively as cell binding agents.

Preparation of Cytotoxic Agents (Conjugates)

Conjugates of the analogues and derivatives of CC-1065 of the invention with a cell binding agent can be formed using any techniques presently known or later developed. An indolyl, benzofuranyl, bis-indolyl, bis-benzofuranyl, indolyl-benzofuranyl, or benzofuranyl-indolyl derivative coupled to CPI or CBI can be prepared to contain a free amino group (for example, starting with compound 10) and then linked to an antibody or other cell binding agent via an acid labile linker, or is a photolabile linker. The cytotoxic compounds can be condensed with a peptide and subsequently linked to a cell binding agent to produce a peptidase labile linker. Cytotoxic compounds can be prepared to contain a primary hydroxyl group (for example, starting with compound 12), which can be succinylated and linked to a cell binding agent to produce a conjugate that can be cleaved by intracellular esterases to liberate free drug. Most preferably, the cytotoxic compounds are treated to create a free or protected thiol group, and then one or many disulfide or thiol containing derivatives are covalently linked to the cell binding agent via disulfide bond(s).

Representative conjugates of the invention are conjugates of analogues or derivatives of CC-1065 and antibodies, antibody fragments, epidermal growth factor (EGF), melanocyte stimulating hormone (MSH), thyroid stimulating hormone (TSH), estrogen, estrogen analogues, androgen, and androgen analogues.

Representative examples of the preparation of various conjugates of analogues and derivatives CC-1065 and cell binding agents are described below.

Figure 5A:
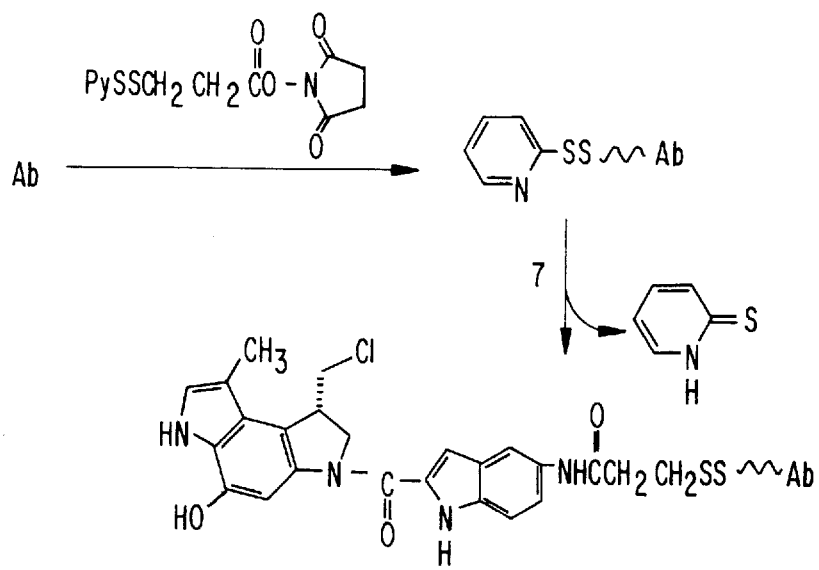
FIGS. 5A and 5B are diagrams of methods of preparing the conjugates according to the present invention.

Disulfide linkers: Antibody N901 which binds to the CD-56 antigen that is expressed on the surface of small cell lung cancer cells {J. D. Griffin, T. Hercend, R. Beveridge & S. F. Schlossman, *J. Immunol,* 130:2947 (1983)} was used for the preparation of conjugates. The antibody was modified with N-succinimidyl-3-pyridyldithio propionate as previously described {J. Carlsson, H. Drevin & R. Axen, *Biochem. J.,* 173:723 (1978)} to introduce, on the average, 4 pyridyldithio groups per antibody molecule. The modified antibody was reacted with the thiol-containing CC-1065 analogue 7 to produce a disulfide-linked conjugate. The number of drug molecules linked was in close agreement with the number of pyridyldithio groups that had been introduced into the antibody molecule. The bis-indolyl-CPI drug 20 was conjugated to antibodies in a similar manner. (See method A, FIG. 5A.)

Figure 5B:
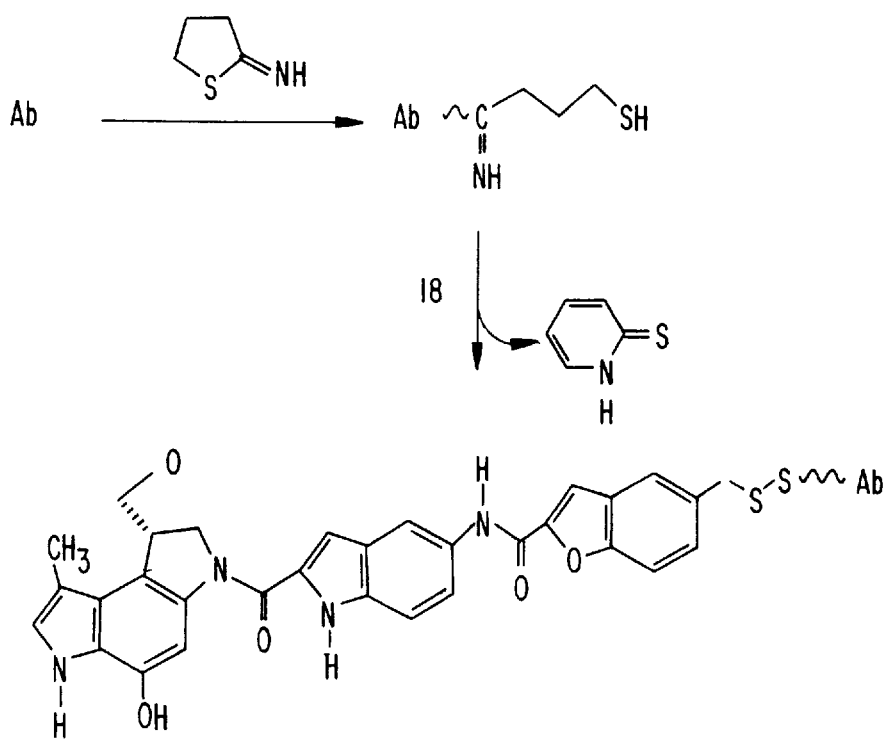

In order to prepare conjugates of the activated disulfide-containing indolyl-benzofuranyl CPI derivative 18 (FIG. 3C), the antibody was modified with 2-iminothiolane as previously described {J. M. Lambert et al, *J. Biol. Chem.,* 260; 12035 (1985)} to introduce, on the average, 4 to 6 sulfhydryl groups per antibody molecule. Reaction with the drug 18 led to the production of conjugates containing, on the average, 3 to 4 molecules of drug linked per molecule of antibody. (See Method B, FIG. 5B.)

Acid-Labile Linkers: CPI can be coupled to an indolyl, benzofuranyl, bis-indolyl, bis-benzofuranyl, or indolyl-benzofuranyl, or benzofuranyl-indolyl derivative bearing a protected amino group containing substituent at C-5 of the terminal indolyl or benzofuranyl moiety. The protecting group can be a tert-butyloxycarbonyl or a biphenylpropyloxycarbonyl functionality that can be cleaved under mild acidic conditions to generate the free amino group. This amino group containing CC-1065 analogue or derivative can be linked to antibodies and other cell binding agents via an acid labile linker as previously described. {W. A. Blattler et al, *Biochemistry* 24, 1517–1524 (1985); U.S. Pat. Nos. 4,542,225, 4,569,789, 4,618,492, 4,764,368}.

Similarly, CPI can be coupled to an indolyl, benzofuranyl, bis-indolyl, bis-benzofuranyl, indolyl-benzofuranyl, or benzofuranyl-indolyl derivative bearing a protected hydrazide group containing substituent at C-5 of the terminal indolyl or benzofuranyl moiety. Again the protecting group can be a tert-butyloxycarbonyl or biphenylpropyloxycarbonyl functionality that can be cleaved under mild acidic conditions to generate the free hydrazide. This hydrazido group containing CC-1065 analogue or derivative can be linked to the carbohydrate portion of antibodies and other cell binding agents via an acid labile hydrazone linker {for examples of hydrazone linkers see B. C. Laguzza et al, *J. Med. Chem.*, 32, 548–555 (1989); R. S. Greenfield et al, *Cancer Res.*, 50, 6600–6607 (1990)}.

Photo-Labile Linkers: The amino group containing CC-1065 analogues or derivatives described above can be linked to antibodies and other cell binding agents via a photolabile linker as previously described {P. Senter et al, *Photochemistry and Photobiology*, 42, 231–237 (1985); U.S. Pat. No. 4,625,014}.

Peptidase-Labile Linkers: The amino group containing CC-1065 analogues or derivatives described above can also be linked to cell binding agents via peptide spacers. It has been previously shown that short peptide spacers between drugs and macromolecular protein carriers are stable in serum but are readily hydrolyzed by intracellular peptidases {A. Trouet et al, *Proc. Natl. Acad. Sci.*, 79, 626–629 (1982)}. The amino group containing CC-1065 analogues or derivatives can be condensed with peptides such as Ala-Leu, Leu-Ala-Leu and Ala-Leu-Ala-Leu (SEQ ID NO:1) using condensing agents such as 1-ethyl-3-(3-dimethylaminopropyl)carbodiimide-HCl (EDC-HCl) to give a peptide derivative that can be linked to cell binding agents.

Esterase-Labile Linkers: CPI can be coupled to an indolyl, benzofuranyl, bis-indolyl, bis-benzofuranyl, or indolyl-benzofuranyl derivative bearing a hydroxy alkyl group containing substituent at C-5 of the terminal indolyl or benzofuranyl moiety. This CC-1065 analogue or derivative can be succinylated with succinic anhydride and then linked to a cell binding agent to produce a conjugate that can be cleaved by intracellular esterases to liberate free drug. {For examples see E. Aboud-Pirak et al, *Biochem Pharmacol.*, 38, 641–648 (1989)}.

The conjugates made by the above methods can be purified by standard column chromatography or by HPLC.

Preferably conjugates between monoclonal antibodies or cell binding agents and analogues or derivatives of CC-1065 are those that are joined via a disulfide bond, as discussed above, that are capable of delivering CC-1065 or analogues thereof. Such cell binding conjugates are prepared by known methods such as modifying monoclonal antibodies with succinimidyl pyridyl-dithiopropionate (SPDP) {Carlsson et al, 173 *Biochem. J.* 723–737 (1978)}. The resulting thiopyridyl group is then displaced by treatment with thiol containing CC-1065 or analogues thereof to produce disulfide linked conjugates. Alternatively, in the case of the aryldithio-CC-1065 analogues or derivatives, the formation of the cell binding conjugate is effected by direct displacement of the aryl-thiol of the CC-1065 derivatives by sulfhydryl groups previously introduced into antibody molecules. Conjugates containing 1 to 10 CC-1065 drugs linked via a disulfide bridge are readily prepared by either method.

More specifically, a solution of the dithiopyridyl modified antibody at a concentration of 1 mg/ml in 0.1 M potassium phosphate buffer, at pH 7.0 containing 1 mM EDTA is treated with the thiol-containing CC-1056 or analogues thereof (1.25 molar equivalent/dithiopyridyl group). The release of thiopyridine from the modified antibody is monitored spectrophotometrically at 343 nm and is complete in about 30 min. The antibody-CC-1065 conjugate is purified and freed of unreacted drug and other low molecular weight material by gel filtration through a column of SEPHADEX G-25(Cross-linked dextrans). The number of CC-1056 molecules or CC-1056 analogue molecules bound per antibody molecule can be determined by measuring the ratio of the absorbance at 252 nm and 280 nm. An average of 1–10 CC-1065 molecules or analogues thereof/antibody molecule can be linked via disulfide bonds by this method.

Conjugates between antibodies and analogues or derivatives of CC-1065 with non-cleavable links can also be prepared. The antibody can be modified with crosslinking reagents such as succinimidyl 4-(N-maleimidomethyl) cyclohexane-1-carboxylate (SMCC), sulfo-SMCC, m-maleimidobenzoyl-N-hydroxysuccinimide ester (MBS), sulfo-MBS or succinimidyl-iodoacetate, as described in the literature, to introduce 1–10 reactive groups. See, Yoshitake et al, 101 *Eur. J. Biochem.* 395–399 (1979); Hashida et al, *J. Applied Biochem.* 56–63 (1984); and Liu et al, 18 *Biochem.* 690–697 (1979). The modified antibody is then reacted with the thiol containing analogue or derivative of CC-1065 to produce a conjugate. The conjugate can be purified by gel filtration through a SEPHADEX G-25 column.

The modified antibodies are treated with the thiol containing CC-1065 (1.25 molar equivalent/maleimido group). The mixtures are incubated for about 1 hour at about 4° C. The conjugates between antibodies and analogues or derivatives of CC-1065 are purified by gel filtration through a SEPHADEX G-25 column. Typically, an average of 1–10 CC-1065 molecules or analogues/antibody are linked.

A preferred method is to modify antibodies with succinimidyl-4-(N-maleimidomethyl)-cyclohexane-1-carboxylate (SMCC) to introduce maleimido groups followed by reaction of the modified antibody with the thiol containing analogues or derivatives of CC-1065 to give a thioether linked conjugates. Again conjugates with 1 to 10 drug molecules per antibody molecule result.

In Vitro Cytotoxicity of Conjugates Between Cell Binding Agents and Analogues or Derivatives of CC-1065

Cytotoxicity of the analogues and derivatives of CC-1065 and their conjugates with cell binding agents to non-adherent cell lines such as Namalwa and SW2 can be measured by back-extrapolation of cell proliferation curves as described in Goldmacher et al, 135 *J. Immunol.* 3648–3651 (1985). Cytotoxicity of these compounds to adherent cell lines such as A-375 and SCaBER can be determined by clonogenic assays as described in Goldmacher et al, 102 *J. Cell Biol.* 1312–1319 (1986).

Therapeutic Agent and Method for Killing Selected Cell Populations

The present invention also provides a therapeutic agent for killing selected cell populations comprising:

(a) a cytotoxic amount of one or more of the above-described analogues or derivatives of CC-1065 linked to a cell binding agent, and (b) a pharmaceutically acceptable carrier, diluent or excipient.

Similarly, the present invention provides a method for killing selected cell populations comprising contacting a cell population or tissue suspected of containing cells from said selected cell population with a cytotoxic amount of a cytotoxic agent comprising one or more of the above-described analogous or derivatives of CC-1065 linked to a cell binding agent.

The cytotoxic agent is prepared as described above.

Suitable pharmaceutically acceptable carriers, diluents, and excipients are well known and can be determined by those of skill in the art as the clinical situation warrants.

Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The method for killing selected cell populations can be practiced in vitro, in vivo, or ex vivo.

Examples of in vitro uses include treatments of cell cultures in order to kill all cells except for desired variants that do not express the target antigen; or to kill variants that express undesired antigen.

The conditions of non-clinical in vitro use are readily determined by the skilled artisan.

Examples of ex vivo uses include treatments of autologous bone marrow prior to their transplant into the same patient in order to kill diseased or malignant cells: treatments of bone marrow prior to their transplantation in order to kill competent T cells and prevent graft-versus-host-disease (GVHD).

For clinical ex vivo use to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent GVHD, treatment can be carried out as follows. Bone marrow is harvested from the patient or other individual and then incubated in medium containing serum to which is added the cytotoxic agent of the invention, concentrations range from about 10 $\mu$M to 1 pM, for about 30 minutes to about 48 hours at about 37° C. The exact conditions of concentration and time of incubation (=dose) are readily determined by the skilled artisan. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels or as a lyophilized solid that can be redisolved in sterile water for injection. Examples of suitable protocols of conjugate administration are as follows. Conjugates are given daily for 5 days either as an i.v. bolus each day for 5 days, or as a continuous infusion for 5 days. Bolus doses are given in 50 to 100 ml of normal saline to which human serum albumin (e.g. 0.5 to 1 mL of a concentrated solution of human serum albumin, 100 mg/mL) has been added. Continuous infusions are given in 250 to 500 ml of normal saline, to which, e.g., 2.5 to 5 mL of the above concentrated solution of human serum albumin has been added, per 24 hour period. Dosages will be 10 $\mu$g to 100 mg/kg of body weight per day, i.v. (range of 1 ng to 10 mg/kg per day). One to four weeks after treatment, the patient may receive a second course of treatment. Specific clinical protocols with regard to route of administration, excipients, diluents, dosages, times, etc., can be determined by the skilled artisan as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; melanomas; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc,; bacterial infection; and parasite infections, such as giardiasis, amoebiasis, schistosomiasis, and others as determined by one skilled in the art.

EXAMPLES

The invention will now be illustrated by reference to non-limiting examples. Unless otherwise stated, all percents, ratios, parts, etc. are by weight.

MATERIALS AND METHODS

Melting points were measured using an Electrothermal apparatus and are uncorrected. NMR spectra were recorded either on a Hitachi 1100 continuous wave (60 MHz) instrument or on a Bruker AM300 (300 MHz) spectrometer. Chemical shifts are reported in ppm relative to TMS as an internal standard. Ultraviolet spectra were recorded on a Hitachi U1200 spectrophotometer. HPLC was performed using a Rainin HPLC system equipped with a Gilson variable wavelength detector and a Waters RADIALPAK, (a reverse phase C-18 column). Thin layer chromatography was performed on Analtech GF silica gel TLC plates. Silica gel for flash column chromatography was from Baker. Tetrahydrofuran was dried by distillation over lithium aluminum hydride. Dimethylactamide and dimethylformamide were dried by distillation over calcium hydride under reduced pressure. All other solvents used were reagent grade or HPLC grade.

Human small cell lung cancer cell line SW2 was obtained from the Dana-Farber Cancer Institute. Human cancer cell lines Namalwa (ATCC#CRL 1432), A-375 (ATCC#CRL 1619, and SCaBER (ATCC HTB 3) were obtained from the American Type Culture Collection (ATCC), Bethesda, Md. respectively.

Example I

SYNTHESIS OF MONO-INDOLYL CC-1065 ANALOGUE 7

Mono-indolyl CC-1065 analogue 7 was synthesized according to Scheme 1 shown in FIG. 2.

3-(phenyldithio)propionic acid (4)

Diphenyldisulfide (9.33 g, 42.6 mmol) was dissolved in THF (40 mL) and treated sequentially with a solution of 3-mercaptopropionic acid (1.51 g, 14.2 mmol) in methanol (40 mL) and 10M NaOH (1.4 mL.). The reaction mixture was stirred under a nitrogen atmosphere at room temperature for 3 h. The solvents were then evaporated under reduced pressure and the white residue was redissolved in ethyl acetate and purified by flash chromatography on silica gel. The product was eluted with ethyl acetate:hexane containing 5% acetic acid to give 4 as a white solid (1.82 g, 60%), mp 58°–59° C. NMR (CDCl$_3$) $\delta$2.5–3.0 (m, 4H), 7.1–7.6 (m, 5H) and 10.8 (s, 1H).

5-[(3-Phenyldithio)propionylamino]-indole-2-carboxylic acid (5)

A solution of 4 (535 mg, 2.50 mmol) in dry THF (10 mL) was cooled to –23° C. under an atmosphere of argon. Triethylamine (253 mg, 2.50 mmol) and isobutylchloroformate(340 mg, 2.50 mmol) were added and the reaction mixture was stirred at this temperature for 30 min. A solution of 5-amino-indole-2-carboxylic acid {M. A. Warpehoski et al, 31, *J. Med. Chem.,* 590–603 (1988) and S. M. Parmerter et al, 80, *J. Med. Chem. Soc.,* 4621 (1958)} (545 mg, 3.1 mmol) in dry DMF (2 mL) was added and the reaction mixture was allowed to warm to room temperature and then was stirred for an additional 45 min. The precipitate was then removed by filtration and the filtrate evaporated under reduced pressure to give a brown residue. Column chromatography on silica gel eluting with ethyl acetate:hexane containing 5% acetic acid gave compound 4 as a tan colored product (185 mg, 20%). NMR (DMSO-d$_6$) $\delta$2.27 (t,2H, J=7 Hz.), 3.06 (t, 2H, J=7 Hz), 7.00 (s, 1H), 7.1–7.7 (m, 8H), 7.98 (s, 1H), 9.92 (s, 1H), 11.62 (s, 1H).

Mono-indolyl CC-1065 analogue 6. CPI was coupled to carboxylic acid 5 and the product was purified as previously described {M. A. Warpehoski et al, 31, *J. Med. Chem.*, 590–603 (1988)} NMR (acetone $d_6$) δ2.42 (s, 3H), 2.83 (t, 2H, J=7 Hz), 3.15 (t, 2H, J=7 Hz), 3.50–3.65 (m, 1H), 3.85–4.20 (m, 2H), 4.50–4.85 (m, 2H), 7.00–8.95 (m, 11H), 8.16 (s, 1H), 9.17 (s, 1H), 9.93 (s, 1H), 10.75 (s, 1H)

Mono-indolyl CC-1065 analogue 7. A sample of disulfide 6 (1.4 μmol) was dissolved in acetonitrile (0.26 mL.) and cooled to 4° C. under an argon atmosphere. A solution of dithiothreitol (1.5 μmol in 0.1M potassium phosphate buffer pH 7.5 (0.06 mL) was added and the progress of the reaction (which was complete in 1 h) was monitored by HPLC using a Waters RADIALPAK reverse phase C-18 column and eluting with a gradient of acetonitrile:water (50% $CH_3CN$ 0–8 min, 50–100% $CH_3CN$ 8–12 min, flow rate=1.5 mL/min.) The starting material 6 had a retention time of 12.3 min while the product 7 eluted at 5.7 min. The thiol content of 7 was determined using Ellman's colorimetric assay and correlated exactly with the concentration of drug as determined spectrophotometrically.

Example II

SYNTHESIS OF INDOLYL-BENZOFURANYL CC-1065 ANALOGUE 18

Indolyl-benzofuranyl-CC-1065 analogue 18 was synthesized according to schemes 2a, 2b and 2c shown in FIGS. 3A, 3B and 3C.

t-Butyl 5-nitroindole-2-carboxylate (9)

To a stirred solution of ethyl 5-nitroindole-2-carboxylate (8) (4.3 g, 19.5 mmol) in 100 mL THF-methanol (1:1, v/v), at room temperature under argon, was added a solution of NaOH (12 g, 300 mmol) in 300 mL water. The resulting deep red-brown solution was stirred for 3 h, then quenched by acidification to pH 1 with dilute HCl. Precipitated product was collected by vacuum filtration and the remaining dissolved product was extracted with THF:ethyl acetate (1:1 v/v). The precipitate was dissolved in THF and this solution was combined with the organic layers from the extractions. Drying over magnesium sulfate, and evaporation of the solvent afforded 5-nitroindole-2-carboxylic acid (3.6 g, 90% yield) as a light brown solid: NMR (acetone $d_6$) δ7.0–9.0 (m,4H), δ9.5 (s, 1H), δ12.5 (s, 1H). To a stirred solution of 5-nitroindole-2-carboxylic acid (3.1 g, 15 mmol) in 150 mL THF, under argon, was added oxalyl chloride (4.8 g, 37.6 mmol) followed by 0.1 mL of DMF which caused a vigorous evolution of gas. After 40 min, the reaction mixture was evaporated to dryness. The resulting solid was redissolved in 100 mL THF and cooled to −23° C. and stirred under argon. A solution of potassium t-butoxide (1.0M in THF, 45 mL, 45 mmol) was then added dropwise over 30 min, and stirring was continued for an additional 20 min. The reaction was quenched with 5 volumes of water, neutralized with dilute HCl, and extracted with ethyl acetate. The organic extracts were washed with saturated aqueous sodium bicarbonate and water, then dried over magnesium sulfate, filtered, and concentrated to afford 6 (3.24 g, 83% yield) as a brown solid:NMR (acetone-$d_6$) δ1.6 (s, 9H), δ7.4–8.9 (m, 5H).

t-Butyl 5-aminoindole-2 carboxylate (10)

A flask was charged with 9 (3.5 g, 13.3 mmol) and 100 mL dry THF, and purged with argon. To this solution was then added palladium hydrogenation catalyst (10% on carbon, 0.6 g) and hydrogen was bubbled into the reaction mixture for 2.5 days. The catalyst was removed by filtration and the solvent was evaporated to give 10 (2.8 g, 91% yield) as a brown solid: NMR (acetone-$d_6$) δ1.6 (s, 9H), δ6.6–7.6 (m, 4H).

Note: This product is unstable, but can be stored under an inert atmosphere at −20° C. in the dark.

t-Butyl 5-(bromomethyl)benzofuran-2-carboxylate (13)

5-Methylbenzofuran-2-carboxylic acid (11) was first converted to its t-butyl ester as follows. To a stirred solution of 11 (20 g, 114 mmol) in 250 mL dry THF, under argon, was added oxalyl chloride (45 g, 356 mmol) and 0.25 mL DMF, which caused a vigorous evolution of gas. After 40 min, the solution was evaporated to dryness. The solid residue was redissolved in 250 mL dry THF and cooled to −23° C. while being stirred under argon. A solution of potassium t-butoxide (1.0M in THF, 280 mL, 280 mmol) was then added dropwise over 1 h. The reaction mixture was poured into 600 mL water, then extracted with ethyl acetate. The organic extracts were washed with saturated aqueous sodium bicarbonate and water, dried over magnesium sulfate, and evaporated to give the ester (24.4 g, 93% yield) as a yellow liquid that solidified on cooling to −20° C.: NMR ($CDCl_3$) δ1.6 (s, 9H), δ2.4 (s, 3H), δ7.1–7.6 (m, 4H).

To a stirred solution of this ester (10 g, 43.1 mmol) in 100 mL distilled carbon tetrachloride were added N-bromosuccinimide (9.2 g, 51.7 mmol) and benzoylperoxide (0.2 g, 0.81 mmol). The reaction mixture was heated at reflux for 1 h. The progress of the reaction was monitored by NMR (methyl: δ2.4; bromomethyl: δ4.6; dibromomethyl: δ6.8) because it is important to stop the reaction before significant formation of the dibrominated compound has occurred. Precipitated succinimide was filtered from the solution, and the filtrate was washed sequentially with water, saturated aqueous sodium bicarbonate, and again water. The carbon tetrachloride solution was dried over magnesium sulfate, filtered and evaporated to give 12 (12.9 g, 96% yield) as a yellow-white solid: NMR ($CDCl_3$) δ1.6 (s,9H), δ4.6 (s, 2H), δ7.3–7.9 (m, 4H).

t-Butyl 5-(S-acetylthiomethyl)benzofuran-2-carboxylate (13)

To a stirred solution of 12 (10 g. 30.6 mmol) in 100 mL dry acetone, under argon at room temperature, was added potassium thioacetate (6.11 g. 53.5 mmol). After 3.5 h, the reaction mixture was treated with 400 mL saturated aqueous sodium bicarbonate and extracted with chloroform. The chloroform layer was washed with bicarbonate solution and water, then dried over magnesium sulfate, filtered, and concentrated to give a thick black oil. The crude product was purified by chromatography on a silica gel column, eluting with ethyl acetate:hexane (10:90) to afford 13 (5.2 g. 55% is yield) as a pale red solid: NMR (acetone-$d_6$) δ1.6 (s, 9H), δ2.3 (s, 3H), δ4.2 (s, 2H), δ7.2–7.7 (m, 4H).

t-Butyl 5-(2-pyridyldithiomethyl)benzofuran-2-carboxylate (14)

A solution of 13 (1.0 g, 3.3 mmol) in 50 mL absolute ethanol was stirred under argon at room temperature, and treated with a solution of sodium borohydride (2.5 g, 65 mmol) in 75 mL ethanol. When a TLC analysis (silica gel, chloroform:hexanes 60:40) of the reaction mixture showed no remaining starting ester (~2 h), the reaction mixture was cooled to 0° C. and treated with 30 mL water. The pH of the solution was lowered to 4 by the addition of glacial acetic acid.

The solution was then brought to pH 5 by the addition of 3M NaOH and a solution of 2-pyridyl-disulfide (2.87 g, 13 mmol) in 10 mL absolute ethanol was added and the reaction mixture stirred for 2 h at room temperature.

The reaction was quenched by addition of saturated aqueous sodium bicarbonate and the mixture was extracted with chloroform. The chloroform layer was washed with sodium bicarbonate solution and water, then dried over magnesium sulfate, filtered, and evaporated. The crude product was then purified by chromatography on a silica gel column, eluting with ethyl acetate:hexane (20:80). The pure product 14 was recovered as a white solid: NMR (CDCl$_3$) δ1.6 (s, 9H), δ4.1 (s, 2H), δ6.8–7.6 (m, 7H), δ8.3–8.5 (m, 1H).

5-(2-pyridyldithiomethyl)benzofuran-2-carboxylic acid (15)

To 15 mL trifluoroacetic acid at 0° C., stirred under argon, was added ester 14 (2.2 g, 5.9 mmol). After 1.5 h, the trifluoroacetic acid was evaporated from the reaction mixture to give 16 (1.8 g, 97% yield) as a white solid: NMR (DMSO-d$_6$) δ4.3 (s, 2H), δ7.0–7.8 (m, 7H), δ8.3–8.5 (m, 1H).

t-Butyl 5-{[5-(2-pyridyldithiomethyl)benzofuran-2-ylcarbonyl]amino}indole-2-carboxylate (16)

A stirred solution of 15 (247 mg, 0.78 mmol) in 30 mL dry THF at room temperature under argon, was treated sequentially with solutions of dicyclohexylcarbodiimide (177 mg, 0.86 mmol) in 5 mL methylene chloride, 4-(dimethylamino)-pyridine (29 mg, 0.23 mmol) in 2 mL methylene chloride, and 10 (200 mg, 0.86 mmol) in 5 mL methylene chloride. The reaction mixture was stirred overnight. Dicyclohexylurea was filtered from the reaction mixture, and the filtrate was washed with water, cold 0.1M HCl, saturated aqueous sodium bicarbonate, and water. The organic solution was dried over magnesium sulfate, filtered, and concentrated to give a dark oil. The crude product was further purified by chromatography on a silica gel column, eluting with ethyl acetate:hexanes to give 16 as an off-white solid: NMR (acetone-d$_6$) δ1.6 (s, 9H), δ4.3 (s, 2H), δ7.0–8.6 (m, 12H).

5-{[5-2-pyridyldithiomethyl)benzofuran-2-yl-carbonyl]amino}indole-2-carboxylic acid (17)

To 4 mL trifluoroacetic acid, cooled to 0° C. and stirred under argon, was added 16 (120 mg, 0.23 mmol). After 2 h, trifluoroacetic acid was removed under reduced pressure to give 15 as an off-white solid: NMR (acetone-d$_6$) d 4.3 (2,2H), δ7.3–8.7 (m, 12H).

Indolyl-benzofuranyl-CC-1065 analogue 18. CPI was coupled with 17 in the presence of EDC as previously described to give 18. Analysis of 18 on a Waters reverse-phase C-18 HPLC column using mixtures of acetonitrile and water as eluent (program: 0–4 min, 60% CH$_3$CN;4–5 min, 0–100% CH$_3$CN; 5–15 min, 100% CH$_3$CN; flow rate 1.5 ml/min) gave a single peak eluting at 8.2 min.

Example III

SYNTHESIS OF BIS-INDOLYL CC-1065 ANALOGUE 22

Bis-indolyl-CC-1065 analogue 22 was synthesized according to Scheme 3 shown in FIG. 4.

t-Butyl (3'-phenyldithiopropionyl)-5-aminoindole-2-carboxylate (19)

To a stirred solution of 3-phenyl-dithiopropionic acid (4) (1.40 g, 6.54 mmol) in anhydrous THF (15 mL) at −23° C. was added isobutylchloroformate (0.93 mL, 7.19 mmol) followed immediately by triethylamine (1.01 mL, 7.19 mmol). After 15 min of stirring at −23° C., a solution of t-butyl-5-aminoindole-2-carboxylate (10) (1.52 g, 6.54 mmol) and triethylamine (0.92 mL, 6.54 mmol) in anhydrous THF (15 mL) was added slowly over a period of 5 min. The reaction mixture was stirred for 30 min at −23° C., brought to ambient temperature and stirred for an additional 30 min. The reaction mixture as acidified by addition of 50 mL 0.5M HCl and extracted with ethyl acetate. The organic phase was washed with water, saturated NaHCO$_3$, and again with water, and dried (MgSO$_4$) and concentrated. The residue was chromatographed over silica gel, eluting with a gradient of ethyl acetate in hexanes. The product 19 was obtained as an off-white solid (1.43 g, 51% yield). NMR (acetone-d$_6$) d 1.6 (s, 9H), δ2.9–3.3 (m, 4H), δ7.0–8.1 (m, 9H), δ9.15 (s, 1H).

t-Butyl 5-[(3'-phenyldithiopropionyl)indol-2-yl carbonyl amino]indole-2-carboxylate (20)

The ester 19 (1.4 g, 3.3 mmol) was treated with trifluoroacetic acid (14 mL) at 0° C. under an argon atmosphere. The reaction mixture was stirred at this temperature for 1 hour. The solution was then evaporated to dryness under reduced pressure and the resulting carboxylic acid was used in the next step without further purification.

The carboxylic acid obtained above (250 mg, 0.64 mmol) was dissolved in anhydrous DMF (1 mL), stirred under an argon atmosphere and treated with solutions of amino ester 10 (149 mg, 0.64 mmol) in DMF (0.5 mL) and EDC (124 mg, 0.64 mmol) in DMF (0.5 mL). The reaction mixture was stirred at room temperature for 48 hours. Cold 0.5M HCl (25 mL) was then added and the mixture was extracted with 1:1 (v/v) THF: ethyl acetate (4×50 mL). The combined organic layers were washed sequentially with H$_2$O (4×100 mL), saturated NaHCO$_3$ solution (2×100 mL) and again H$_2$O (2×100 mL). The organic layer was dried (MgSO4), filtered and the solvents evaporated to dryness under reduced pressure. The residue was chromatographed on a silica gel column eluting with acetone: toluene (30:70 v/v) to give the pure product 20 (200 mg, 52% yield). NMR (DMSO-d$_6$) 8.12–7.10 (m, 13H), 3.3–2.77 (m, 4H), 1.58 (S, 9H).

Conversion of 20 to bis-indolyl-CC-1065 analogue 21. The ester 20 was hydrolyzed to the carboxylic acid with trifluoroacetic acid at 0° C. as described above for the hydrolysis of ester 19. The carboxylic acid obtained was coupled to CPI with EDC as previously described {M. A. Warpehoski et al, 31, *J. Med. Chem.*, 590–603 (1988)} to give the bis-indolyl CC-1065 analogue 21. Analysis of 21 by HPLC on a Waters reverse phase C-18 column using mixtures of acetonitrile and water as eluent (program: 60 to 100% CH$_3$CN in 10 minutes, 100% CH$_3$CN for 5 minutes, flow rate 2.5 mL/min) gave a single peak for 21 with a retention time of 10.1 minutes.

Reduction of 21 to thiol-containing CC-1065 analogue 22. A solution of the bis-indolyl-CC-1065 analogue 21 (0.04 μmol) in acetonitrile: THF (0.08 mL) (1:1, v/v) was treated with a solution of dithiothreitol (0.06 μmol) in 0.1M potassium phosphate buffer, pH 7.5 (0.014 mL) containing 2 mM EDTA. The reaction mixture was kept under an argon atmosphere at 4° C. for 4 hours. At this time, an additional portion of dithiothreitol (0.18 μmol) was added. After 30 minutes, the reaction mixture was purified by HPLC (conditions as described above for purification 21). A new peak with a retention time of 8.0 minutes was identified as thiol containing CC-1065 analogue 22. This peak had a characteristic absorption spectrum and assayed positive for thiol using Ellman's assay {G. L. Ellman, 82, *Arch. Biochem. Biophys.*, 70 (1959)}.

Example IV

CONJUGATION OF DRUG TO ANTIBODIES

The conjugation of drugs to antibodies was achieved in the following ways:

Method A. Drug contains a thiol group: The antibody was modified with SPDP [N-succinimidyl-3-(2-pyridyldithio)- propionate] to introduce dithiopyridyl groups. Reaction of the thiol-containing drug with the modified antibody produced disulfide-linked conjugates. (See FIG. 5A).

Method B. Drug contains an activated disulfide group: The antibody was modified with 2-iminothiolane to introduce thiol groups. Reaction of the modified antibody with the drug produced disulfide-linked conjugates. (See FIG. 5B).

Method A. Antibody N901 was modified with SPDP as previously described {J. Carlsson et al, 173 Biochem. J, 723 (1978)} to introduce 4 to 6 dithiopyridyl groups, on the average, per molecule of antibody. A solution of the antibody at a concentration of 4 mg/mL in 0.1M potassium phosphate pH 7.0 containing 2 mM EDTA was treated with a 10-fold molar excess of SPDP in ethanol and the mixture was incubated at 30° C. for 30 min. The modified antibody was purified by gel filtration through a column of SEPHADEX G-25 and then incubated with a 10-fold molar excess of the thiol-containing drug in dimethylacetamide (DMA) such that the final DMA concentration was $\leq 10\%$. The conjugation mixture was incubated under an argon atmosphere in the dark at 20° C. for 3 h and then purified by passage through a SEPHADEX G-25 gel filtration column to remove unconjugated drug and other low molecular weight material. Conjugates containing, on the average, 4 molecules of drug per antibody molecule were obtained by this method.

Method B. Antibody N901 was modified using 2-iminothiolane (2-IT) to introduce, on the average, 4 to 6 thiol groups per antibody molecule as previously described {J. M. Lambert et al, 260 J. Biol. Chem., 12035 (1985)}. A solution of the antibody at a concentration of 4 mg/mL in 0.1M triethanolamine buffer pH 8.0 containing 2 mM EDTA was treated with a solution of 2-iminothiolane (final concentration=1.5 mM) and incubated at 4° C. for 90 min. under an atmosphere of argon. The modified antibody was purified by gel filtration through a column of SEPHADEX G-25. Thiol incorporation was determined using Ellman's assay {82, Arch. Biochem. Biophys., 70 (1959)}. To the modified antibody was added a solution of 16 in DMA such that a ten-fold molar excess of 16 was used, and the final DMA concentration was $\leq 10\%$. The conjugation mixture, which turned cloudy, was incubated under an argon atmosphere in the dark at 20° C. for 3 h. The solution was clarified by centrifugation, and then applied to a SEPHADEX G-25 gel filtration column to remove unreacted drug. The resulting conjugates contained, on the average, 3 to 5 molecules of drug per antibody molecule.

Example V

IN VITRO CYTOTOXICITY AND SPECIFICITY OF ANTIBODY-SS-DRUG CONJUGATES

In vitro cytotoxicity of N901-SS-Drug 7. The in vitro cytotoxicity of a disulfide-linked conjugate of the monoindolyl CPI derivative 7 with the antibody N901, containing on the average 3.3 drug molecules per antibody molecule, was measured on antigen positive SW2 cells and antigen negative Namalwa cells. Cells were exposed to the conjugate for 24 h at 37° C., and the surviving fractions of cells were determined using a growth back-extrapolation assay {V. S. Goldmacher et al, 135, J. Immunol., 3648–3651 (1985)}.

Figure 6:
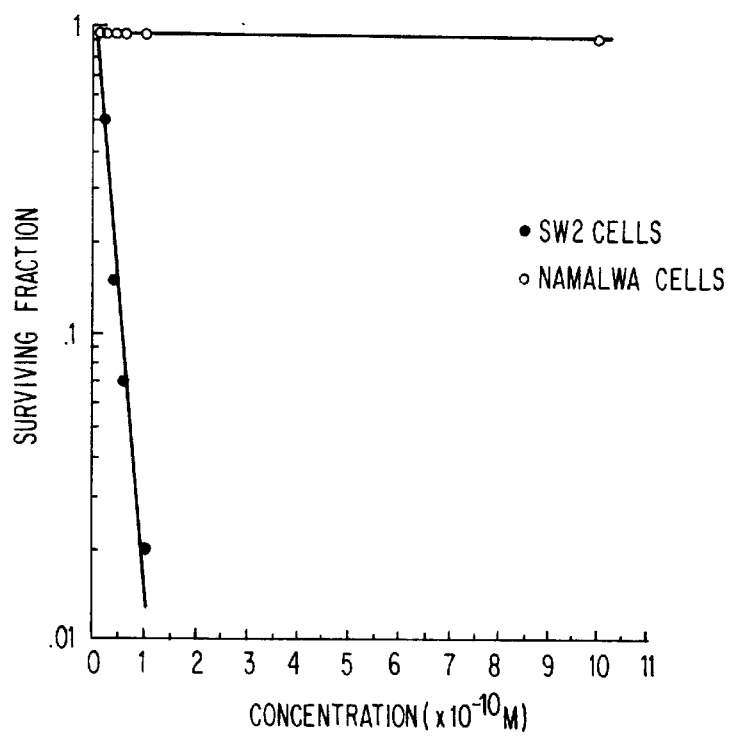
FIG. 6 is a graph showing the in vitro cytotoxicity and specificity of derivative drug 7 conjugate of the present invention toward SW2 and Namalwa cells. The abscissa represents the concentration of conjugate and the ordinate represents the surviving fraction of cells. The closed circles represent data for the antigen positive SW2 cells, and the open circles represent data for the antigen negative Namalwa cells.

The results are shown in FIG. 6. In FIG. 6, the abscissa represents drug concentration and the ordinate represents fraction of surviving cells. Closed circles represent SW2 cells and open circles represent Namalwa cells.

The results show that this conjugate is extremely cytotoxic towards the antigen positive SW2 cells with an $IC_{50}$ value of $1.4 \times 10^{-11}$M. In contrast, this conjugate is non-toxic even at $1 \times 10^{-9}$M to the antigen negative Namalwa cells demonstrating the specificity of the cytotoxic effect. Addition of a 1000-fold excess of unconjugated antibody abolished the cytotoxicity towards SW2 cells, further demonstrating the antigen specificity of the cytotoxic effect.

The in vitro cytotoxicity of the above-described disulfide-linked conjugate was also measured on antigen positive A-375 cells and antigen negative ScABER cells. Cells were exposed to the conjugate for 24 h at 37° C., and the surviving fractions of cells were determined using a clonogenic assay {C. F. Scott et al, 25, Cancer Immunol Immunother., 31–40 (1987)}.

Figure 7:
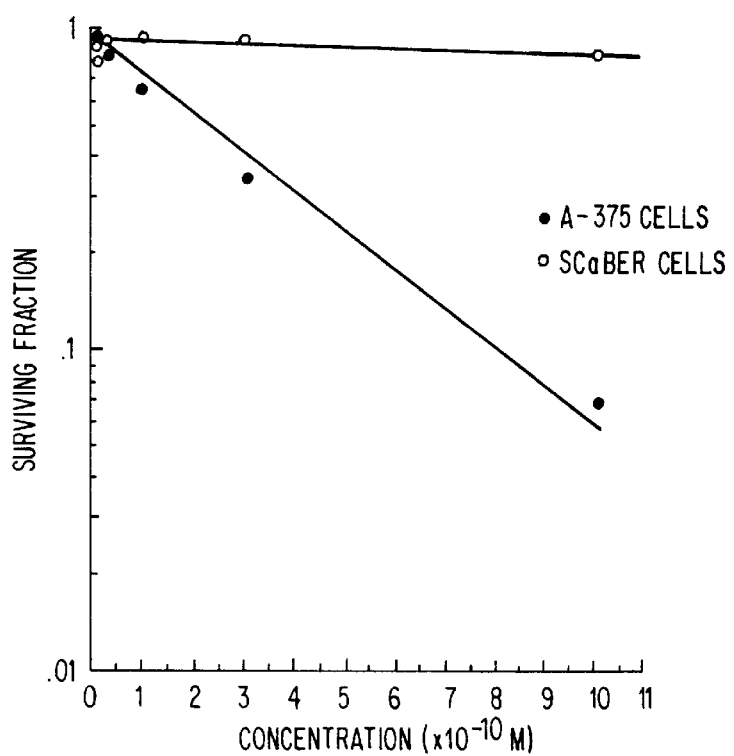
FIG. 7 is a graph showing the in vitro cytotoxicity and specificity of derivative drug 7 conjugate of the present invention toward the antigen positive A-375 and the antigen negative SCaBER cells. The abscissa represents the concentration of conjugate, and the ordinate represents the surviving fraction of cells. The closed circles represent data for the A-375 cells, and the open circles represent data for the SCaBER cells.

The results are shown in FIG. 7. In FIG. 7, the abscissa represents drug concentration and the ordinate represents fraction of surviving cells. Closed circles represent A-375 cells and open circles represent ScABER cells.

The results show that this conjugate was somewhat less cytotoxic towards the melanoma cell line A-375 ($IC_{50}=2\times 10^{-10}$M, FIG. 7). The diminished cytotoxicity is consistent with the fact that this cell line expresses much fewer antigens for N901. Here again the conjugate is non-toxic towards the antigen negative human bladder cancer cell line SCaBER (surviving fraction=100% at $1 \times 10^{-9}$M).

In vitro cytotoxicity of N901-SS-Drug 18. The in vitro cytotoxicity of a disulfide-linked conjugate of the indolyl-benzofuran CC-1065 analogue 18 with antibody N901, containing on the average only two drug molecules per antibody molecule, was measured on antigen positive SW2 cells and antigen negative Namalwa cells. Cells were exposed to the conjugate for 24 h at 37° C., and the surviving fractions of cells were determined using a growth back-extrapolation assay {V. S. Goldmacher et al, 135, J. Immunol., 3648–3651, 1985)}.

Figure 8:
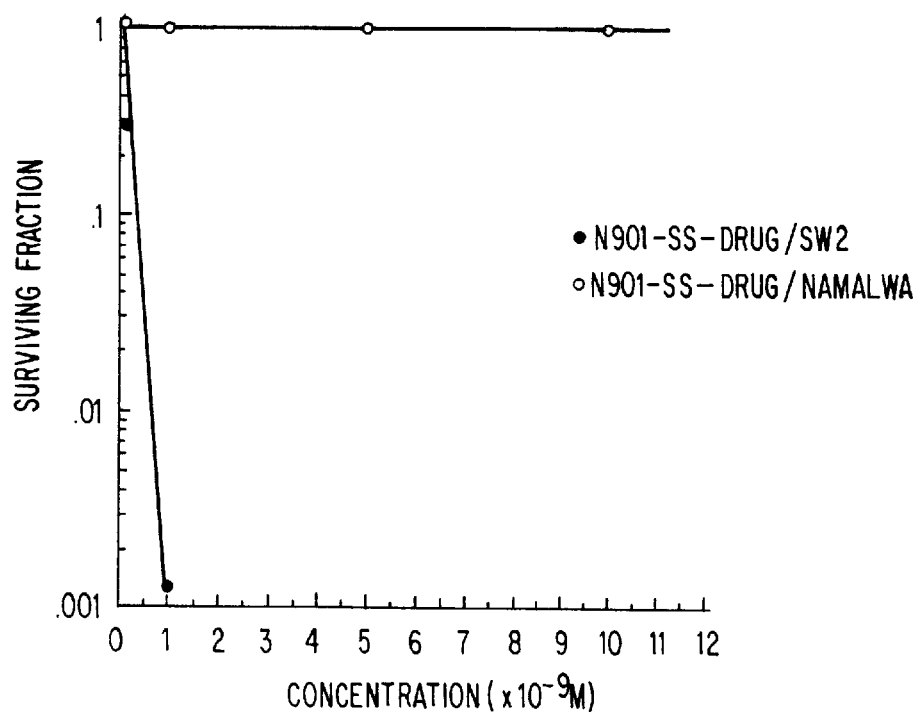
FIG. 8 is a graph showing in vitro cytotoxicity and specificity of the CC-1065 analogue 18 conjugate of the present invention toward SW2 and Namalwa cells. The abscissa represents the concentration of conjugate, and the ordinate represents the surviving fraction of cells. The closed circles represent data for the antigen positive SW2 cells, and the open circles represent data for the antigen negative Namalwa cells.

The results are shown in FIG. 8. In FIG. 8, the abscissa represents drug concentration and the ordinate represents fraction of surviving cells. Closed circles represent SW2 cells and open circles represent Namalwa cells.

The results show that this conjugate is highly cytotoxic towards the antigen positive SW2 cells with an $IC_{50}$ value of $1 \times 10^{-10}$M (99.9% of cells killed at $1 \times 10^{-9}$M) while it is non-toxic to antigen negative Namalwa cells even at a 100-fold higher concentration (at $1 \times 10^{-8}$M) which is the highest concentration tested, 100% of the cells survived.

In vitro cytotoxicity of N901-SS-Drug 22. The in vitro cytotoxicity of a disulfide-linked conjugate of the indolyl-benzofuran CC-1065 analogue 22 with antibody N901, containing on the average only four drug molecules per antibody molecule, was measured on antigen positive SW2 cells and antigen negative Namalwa cells. Cells were exposed to the conjugate for 24 h at 37° C., and the surviving fractions of cells were determined using a growth back-extrapolation assay {V. S. Goldmacher et al, 135, J. Immunol., 3648–3651, 1985)}.

The results are shown in FIG. 9. In FIG. 9, the abscissa represents conjugate or drug concentration and the ordinate represents fraction of surviving cells. The circles represent data for the conjugate for the antigen positive SW2 cells, the triangles represent data for free CC-1065 analogue 22, the squares represent data for conjugate in the presence of free antibody, and the diamonds represent data for the conjugate for the antigen negative Namalwa cells.

The results show that this conjugate is highly cytotoxic towards the antigen positive SW2 cells with an $IC_{50}$ value of $1.9 \times 10^{-11}$M (99.9% of cells killed at $2 \times -10^{9}$M) while it is much less toxic to antigen negative Namalwa cells even at a 100-fold higher is concentration (at $1 \times 10^{-9}$M).

While the invention has been described in detail and with reference to specific embodiments thereof, it will be apparent to one skilled in the art that various changes and modifications can be made therein without departing from the spirit and scope thereof.

What is claimed is:

1. A cytotoxic agent comprising a cell binding agent linked to one or more analogues or derivatives of cyclopropylbenzindole-containing cytotoxic drugs which are internalized by target cells, wherein prior to linking said one or more cyclopropylbenzindole-containing cytotoxic drugs to said cell binding agent said one or more cyclopropylbenzindole-containing cytotoxic drugs are selected from the group consisting of one or more cyclopropylbenzindole-containing cytotoxic drugs formed from an A subunit of the formulae (A-3) or (A-4) covalently linked to a B subunit or a B-C subunit of the formulae (F-1), (F-2), (F-3), (F-4), (F-5), (F-6), (F-7), (F-8), (F-9) or (F-10) via an amide bond from the secondary amino group of the pyrrole moiety of the A subunit to the C-2 carboxyl group of the B subunit, wherein the formulae A-3 and A-4 are as follows:

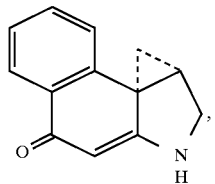

(A-3)

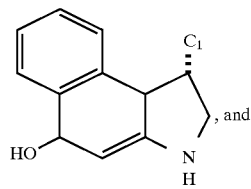

(A-4)

wherein the formulae (F-1) to (F-10) are as follows:

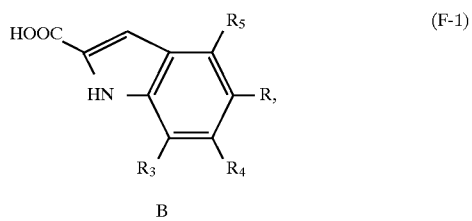

(F-1)

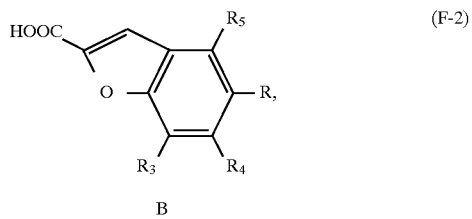

(F-2)

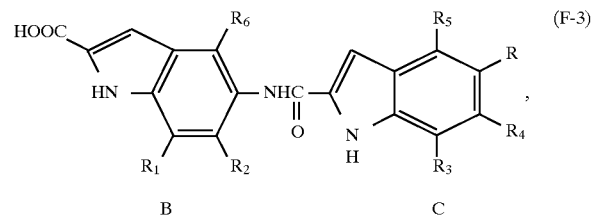

(F-3)

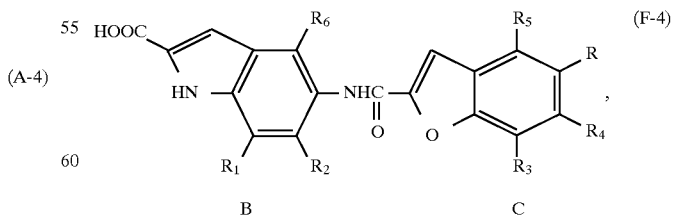

(F-4)

wherein, in a given formula, one of either R and R' or $R_4$ represents a moiety that enables linkage of the one or more cyclopropylbenzindole-containing cytotoxic drugs to a cell binding agent; when R or R' represent moieties that enable linkage, then $R_1$ to $R_6$, which may be the same or different, represent hydrogen, $C_1$–$C_3$ linear alkyl, methoxy, hydroxyl, primary amino, secondary amino, tertiary amino, or amido; and when $R_4$ represents a moiety that enables linkage, R, $R_1$, $R_2$, $R_3$, $R_4$, $R_5$ and $R_6$, which may be the same or different, represent hydrogen, $C_1$–$C_3$ linear alkyl, methoxy, hydroxyl, primary amino, secondary amino, tertiary amino, or amido, and R' represents $NH_2$, alkyl, o-alkyl, primary amino, secondary amino, tertiary amino, or amido.

2. The cytotoxic agent of claim 1, wherein R and R' represent moieties that enable linkage and $R_1$ and $R_2$ represent hydrogen.

3. The cytotoxic agent of claim 1 or 2, wherein R and R' represent moieties that enable linkage of the one or more cyclopropylbenzindole-containing cytotoxic drugs to a cell binding agent via a disulfide bond.

4. The cytotoxic agent of claim 1 or 2, wherein R represents $NHCO(CH_2)_lSZ_0$, $NHCOC_6H_4(CH_2)_lSZ_0$, or $O(CH_2)_lSZ_0$ and R' represents $(CH_2)_lSZ_0$, $NH(CH_2)_lSZ_0$, or $O(CH_2)_lSZ_0$ wherein:

$Z_0$ represents H or $SR_7$, wherein $R_7$ represents methyl, linear alkyl, branched alkyl, cyclic alkyl, simple or substituted aryl or heterocyclic; and l represents an integer of 1 to 10.

5. The cytotoxic agent of claim 4, wherein $Z_0$ represents hydrogen and l represents 2.

6. The cytotoxic agent of claim 4, wherein $Z_0$ represents $SR_7$, $R_7$ represents heterocyclic, and l represents 1.

7. The cytotoxic agent of claim 6, wherein $R_7$ represents a 2-substituted pyridine group.

8. The cytotoxic agent of claim 1 or 2, wherein R and R' represent moieties that enable linkage of the one or more cyclopropylbenzindole-containing cytotoxic drugs to a cell binding agent via an acid-labile group, a photo-labile group, a peptidase-labile group, or an esterase-labile group.

9. The cytotoxic agent of claim 1 or 2, wherein said cell binding agent is a peptide or a non-peptide.

10. The cytotoxic agent of claim 1 or 2, wherein said cell binding agent is a polyclonal or monoclonal antibody.

11. The cytotoxic agent of claim 10, wherein said cell binding agent is a monoclonal antibody.

12. The cytotoxic agent of claim 10, wherein said cell binding agent comprises at least one binding site of said antibody.

13. The cytotoxic agent of claim 11, wherein said cell binding agent comprises at least one binding site of said antibody.

14. The cytotoxic agent of claim 1 or 2, wherein said cell binding agent is a hormone.

15. The cytotoxic agent of claim 1, wherein said hormone is melanocyte stimulating hormone (MSH) or an analogue thereof.

16. The cytotoxic agent of claim 14, wherein said hormone is thyroid stimulating hormone (TSH) or an analogue thereof.

17. The cytotoxic agent of claim 1 or 2, wherein said cell binding agent is a growth factor.

18. The cytotoxic agent of claim 17, wherein said growth factor is epidermal growth factor (EGF).

19. The cytotoxic agent of claim 17, wherein said growth factor is transforming growth factor alpha (TGF-α).

20. A therapeutic agent for killing selected cell populations in vitro, in vivo, or ex vivo, comprising:

(a) a cytotoxic amount of one or more cytotoxic agents of claim 1, and (b) a pharmaceutically acceptable carrier, diluent, or excipient.

21. The therapeutic agent for killing selected cell population of claim 20, wherein R and R' represent moieties that enable linkages and $R_1$ and $R_6$ represent hydrogen.

22. The therapeutic agent for killing selected cell populations of claim 20 or 21, wherein R and R' represent moieties that enable linkage of the one or more cyclopropylbenzindole-containing cytotoxic drugs to a cell binding agent via a disulfide bond.

23. The therapeutic agent for killing selected cell populations of claim 20 or 21, wherein R represents $NHCO(CH_2)_l SZ_0$, $NHCOC_6H_4(CH_2)_l SZ_0$, or $O(CH_2)_l SZ_0$ and R' represents $(CH_2)_l SZ_0$, $NH(CH_2)_l SZ_0$, or $O(CH_2)_l SZ_0$ wherein:

$Z_0$ represents H or $SR_7$, wherein $R_7$ represents methyl, linear alkyl, branched alkyl, cyclic alkyl, simple or substituted aryl or heterocyclic; and l represents an integer of 1 to 10.

24. The therapeutic agent for killing selected cell populations of claim 23, wherein $Z_0$ represents hydrogen and l represents 2.

25. The therapeutic agent for killing selected cell populations of claim 23, wherein $Z_0$ represents $SR_7$, $R_7$ represents heterocyclic, and l represents 1.

26. The therapeutic agent for killing selected cell populations of claim 25, wherein $R_7$ represents a 2-substituted pyridine group.

27. The therapeutic agent for killing selected cell populations of claim 20 or 21, wherein R and R' represent moieties that enable linkage of the one or more cyclopropylbenzindole-containing cytotoxic drugs to a cell binding agent via an acid-labile group, a photo-labile group, a peptidase-labile group, or an esterase-labile group.

28. The therapeutic agent for killing selected cell populations of claim 20 or 21, wherein said cell binding agent is a peptide or a non-peptide.

29. The therapeutic agent for killing selected cell populations of claim 20 or 21, wherein said cell binding agent is a polyclonal or monoclonal antibody.

30. The therapeutic agent for killing selected cell populations of claim 29, wherein said cell binding agent is a monoclonal antibody.

31. The therapeutic agent for killing selected cell populations of claim 29, wherein said cell binding agent comprises at least one binding site of said antibody.

32. The therapeutic agent for killing selected cell populations of claim 30, wherein said cell binding agent comprises at least one binding site of said antibody.

33. The therapeutic agent for killing selected cell populations of claim 20 or 21, wherein said cell binding agent is a hormone.

34. The therapeutic agent for killing selected cell populations of claim 33, wherein said hormone is a melanocyte stimulating hormone (MSH) or an analogue thereof.

35. The therapeutic agent for killing selected cell populations of claim 33, wherein said hormone is thyroid stimulating hormone (TSH) or an analogue thereof.

36. The therapeutic agent for killing selected cell populations of claim 20 or 21, wherein said cell binding agent is a growth factor.

37. The therapeutic agent for killing selected cell populations of claim 36, wherein said growth factor is epidermal growth factor (EGF).

38. The therapeutic agent for killing selected cell populations of claim 36, wherein said growth factor is transforming growth factor alpha (TFG-α).

39. A method for killing selected cell populations in vitro, in vivo, or ex vivo, comprising contacting a cell population or tissue suspected of containing cells from said selected cell population with a cytotoxic amount of the cytotoxic agent of claim 1.

40. A method for killing selected cell populations of claim 39, wherein R and R' represent moieties that enable linkage and $R_1$ to $R_6$ represent hydrogen.

41. The method for killing selected cell populations of claim 39 or 40, wherein R and R' represent moieties that enable linkage of the one or more cyclopropylbenzindole-containing cytotoxic drugs to a cell binding agent via a disulfide bond.

42. The method for killing selected cell populations of claim 39 or 40, wherein R represents $NHCO(CH_2)_l SZ_0$, $NHCOC_6H_4(CH_2)_l SZ_0$, or $O(CH_2)_l SZ_0$ and R' represents $(CH_2)_l SZ_0$, $NH(CH_2)_l SZ_0$, or $O(CH_2)_l SZ_0$ wherein:

$Z_0$ represents H or $SR_7$, wherein $R_7$ represents methyl, linear alkyl, branched alkyl, cyclic alkyl, simple or substituted aryl or heterocyclic; and l represents an integer of 1 to 10.

43. The method for killing selected cell populations of claim 42, wherein $Z_0$ represents hydrogen and l represents 2.

44. The method for killing selected cell populations of claim 42 wherein $Z_0$ represents $SR_7$, $R_7$ represents heterocyclic, and l represents 1.

45. The method for killing selected cell populations of claim 44, wherein $R_7$ represents a 2-substituted pyridine group.

46. The method of killing selected cell populations of claim 39 or 40, wherein R and R' represent moieties that enable linkage of the one or more cyclopropylbenzindole-containing cytotoxic drugs to a cell binding agent via an acid-labile group, a photo-labile group, a peptidase-labile group, or an esterase-labile group.

47. The method of killing selected cell populations of claim 39 or 40, wherein said cell binding agent is a peptide or a non-peptide.

48. The method of killing selected cell populations of claim 39 or 40, wherein said cell binding agent is a polyclonal or monoclonal antibody.

49. The method of killing selected cell populations of claim 48, wherein said cell binding agent is a monoclonal antibody.

50. The method of killing selected cell populations of claim 48, wherein said cell binding agent comprises at least one binding site of said antibody.

51. The method of killing selected cell populations of claim 49, wherein said cell binding agent comprises at least one binding site of said antibody.

52. The method of killing selected cell populations of claim 39 or 40, wherein said cell binding agent is a hormone.

53. The method of killing selected cell populations of claim 52, wherein said hormone is melanocyte stimulating hormone (MSH) or an analogue thereof.

54. The method of killing selected cell populations of claim 48, wherein said hormone is thyroid stimulating hormone (TSH) or an analogue thereof.

55. The method of killing selected cell populations of claim 39 or 40, wherein said cell binding agent is a growth factor.

56. The method of killing selected cell populations of claim 55, wherein said growth factor is epidermal growth factor (EGF).

57. The method of killing selected cell populations of claim 55, wherein said growth factor is transforming growth factor alpha (TFG-α).

* * * * *

UNITED STATES PATENT AND TRADEMARK OFFICE
CERTIFICATE OF CORRECTION

PATENT NO.   : 5,846,545
DATED        : December 8, 1998
INVENTOR(S)  : Ravi V.J. Chari et al.

It is certified that error appears in the above-identified patent and that said Letters Patent is hereby corrected as shown below:

Title page,

Column 2,
"Other Publications" Line 30, delete "Ravi et al. and insert therefor -- Chari et al. --;
Line 39, delete "Hanada" and insert therefor -- Hanka --;
Line 40, delete "Antiobiotic" andinsert therefor -- Antibiotic --;
Lines 44-45, delete "Duocarmycons" and insert therefor -- Duocarmycins --.

In the Abstract,
Line 1 thereof, delete "Gytotoxic" and insert therefor -- Cytotoxic --.

Figure 1C:
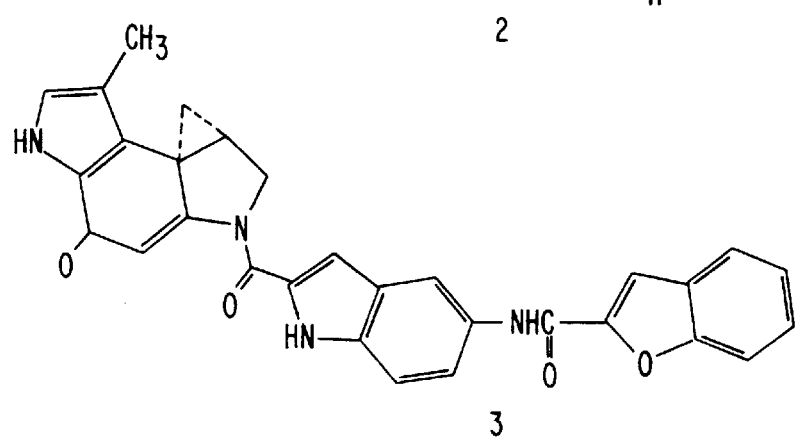

Delete the existing Fig. 1C and insert therefor the following Fig. 1C:

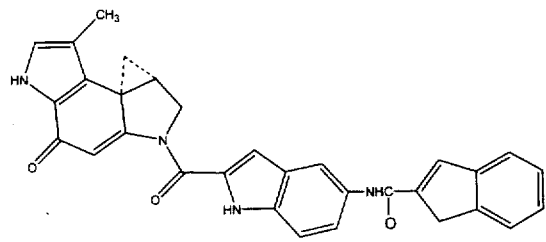

Signed and Sealed this

Ninth Day of October, 2001

Attest:

NICHOLAS P. GODICI
Attesting Officer   Acting Director of the United States Patent and Trademark Office

UNITED STATES PATENT AND TRADEMARK OFFICE
CERTIFICATE OF CORRECTION

PATENT NO.   : 5,846,545
DATED        : December 8, 1999
INVENTOR(S)  : Ravi V.J. Chari et al.

Page 1 of 1

It is certified that error appears in the above-identified patent and that said Letters Patent is hereby corrected as shown below:

Column 17,
Line 62, delete "CC-1056" and insert therefor -- CC-1065 --.

Column 18,
Line 2, delete "CC-1056" and insert therefor -- CC-1065 --;
Line 3, delete "CC-1056" and insert therefor -- CC-1065 --;

Claim 1,
Delete the existing structure A-4 and insert therefor the following structure A-4:

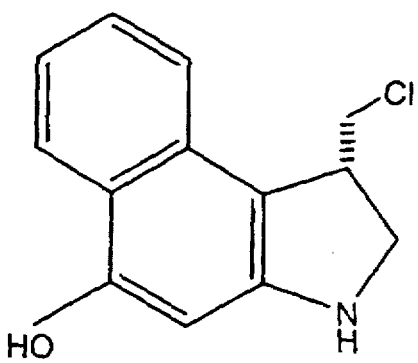

Signed and Sealed this

Twenty-fifth Day of December, 2001

Attest:

JAMES E. ROGAN
Attesting Officer
Director of the United States Patent and Trademark Office

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Ala  Leu  Ala  Leu
1